United States Patent [19]

Ingram et al.

[11] Patent Number: 5,821,093
[45] Date of Patent: Oct. 13, 1998

[54] RECOMBINANT CELLS THAT HIGHLY EXPRESS CHROMOSOMALLY-INTEGRATED HETEROLOGOUS GENES

[75] Inventors: Lonnie O. Ingram; Kazuyoshi Ohta; Brent E. Wood, all of Gainesville, Fla.

[73] Assignee: University of Florida Research Foundation, Inc., Gainesville, Fla.

[21] Appl. No.: 363,868

[22] Filed: Dec. 27, 1994

Related U.S. Application Data

[63] Continuation-in-part of Ser. No. 13,658, Feb. 4, 1993, abandoned, which is a continuation of Ser. No. 624,227, Dec. 7, 1990, abandoned, which is a continuation-in-part of Ser. No. 352,062, May 15, 1989, Pat. No. 5,000,000, which is a continuation-in-part of Ser. No. 239,099, Aug. 31, 1988, abandoned.

[51] Int. Cl.$^6$ .............................. C12P 7/06; C12N 15/63; C12N 1/21; C07H 21/04
[52] U.S. Cl. ...................... 435/161; 435/163; 435/172.3; 435/252.3; 435/252.33; 536/23.2; 536/23.7; 536/24.1
[58] Field of Search ................................. 435/252.3, 161, 435/163, 172.3, 252.33; 536/23.2, 23.7, 24.1

[56] References Cited

PUBLICATIONS

McPartland et al. Isolation and characterization of mutations creating high–efficiency transcription initiation signals within the trp operon of Escherichia coli. Journal of Bacteriology vol. 128 pp. 557–572, 1976.

Hamilton et al. New method for generating deletions and gene replacements in *Escherichia coli* J. Bact. vol. 171 4617–4622, 1989.

Old Chapter 7, Expression in *E. coli* of cloned DNA molecules in Principles of gene manipulation, Blackwell Scientific Publishers, 127–152, 1985.

Sawers et al. Anaerobic regulation of pyruvate fprmate–lyase from *Escherichia coli* K–12 J. Bact. vol. 170 5330–5336, 1988.

Wertheimer et al. Transcriptional patterns for the thrS–infC–rplT operon of *Escherichia coli* Gene vol. 63 309–320, 1988.

Landick et al. Transcription Attenuation, Chapter 77 in *Escherichia coli* and *Salmonella typhimurium* cellular and molecular biology American Society for Microbiology vol. 2 1276–1301, 1987.

Ingram et al. Genetic engineering of ethanol production in *Escherichia coli* Appl. and Environ. Microbiol. vol. 53 2420–2425, 1987.

Alam et al. Anaerobic fermentation balance of *Escherichia coli* as observed by in vivo nuclear magnetic resonance spectroscopy J. Bact. vol. 171 6213–6217, 1989.

Weinstock General recombination in *Escherichia coli* Chapter 60 in *Escherichia coli* and *Salmonella typhimurium* cellular and molecular biology vol. 2 American Society for Microbiology 1034–1043, 1987.

Wood et al. Ethanol production from cellobiose, amorphous cellulose, and crystalline cellulose by recombinant *Klebsiella oxytoca* containing chromosomally integrated *Zymomonas mobilis* genes for ethanol production and plasmids expressing thermostable cellulase genes from *Clostridium thermocellum*. Appl. Environ. Microbiol vol. 58 pp. 2103–2110, 1992.

L. Ingram, "Microbial Tolerance to Alcohols: Role of the Cell Membrane", Trends in Biotechnology, vol. 4, No. 2, Feb. 1986, pp. 1–5.

C. Furlong, "Nutrient Transport Systems of *E. Coli* and *S. Typhimurium*" Osmotic–Shock–Sensitive Transport Systems, Dept. of Genits and Medicin, Center for Inherited Diseases, pp. 768–796.

J. Cronan, Jr. et al., "Cytoplasmic Membrane", *Escherichia Coli* and *Salmonella Typhimurium* Cellular and Molecular Biology, American Society for Microbiology, 1987, pp. 31–55.

B. David et al., "Bacterial Physiology", Microbiology Including Immunology and Molecular Genetics, second edition, p. 64.

G. Gottschalk, "Degradation of Glucose–6–Phosphate to Pyruvate", Bacterial Metabolism, second edition, 1985, p. 17.

T. Tomabene et al., Characterization of the Total Extractable Lipids of *Zymomonas mobilis* var. mobilis, Can. J. Microbiol., vol. 28, 1982, pp. 1107–1118.

Y. Tahara et al., "Isolation of Free Ceramide from *Zymomonas mobilis*", Agric. Biol. Chem., 54(6), pp. 1581–1582.

A. Benschoter et al., "Thermal Tolerance of *Zymomonas mobilis*: Temperature–Induced Changes in Membrane Composition", Applied and Environmental Microbiology, vol. 51, No. 6, Jun. 1986, pp. 1278–1284.

V.C. Carey et al., "Lipid Composition of *Zymomonas mobilis*: Effects of Ethanol and Glucose", Journal of Bacteriology, vol. 154, No. 3, Jun. 1983, pp. 1291–1300.

(List continued on next page.)

Primary Examiner—George C. Elliott
Assistant Examiner—John S. Brusca
Attorney, Agent, or Firm—Hamilton, Brook, Smith & Reynolds, P.C.

[57] ABSTRACT

Recombinant host cells are obtained that comprise (A) a heterologous, polypeptide-encoding polynucleotide segment, stably integrated into a chromosome, which is under transcriptional control of an endogenous promoter and (B) a mutation that effects increased expression of the heterologous segment, resulting in enhanced production by the host cells of each polypeptide encoded by that segment, relative to production of each polypeptide by the host cells in the absence of the mutation. The increased expression thus achieved is retained in the absence of conditions that select for cells displaying such increased expression. When the integrated segment comprises, for example, ethanol-production genes from an efficient ethanol producer like *Zymomonas mobilis*, recombinant *Escherichia coli* and other enteric bacterial cells within the present invention are capable of converting a wide range of biomass-derived sugars efficiently to ethanol.

31 Claims, 8 Drawing Sheets

OTHER PUBLICATIONS

S. Bringer et al., "Influence of Ethanol on the Hopanoid Content and the Fatty Acid Pattern in Batch and Continuous Cultures of *Zymomonas mobilis*", Arch Microbiol, (1985) 140:312–316.

Y. Tahara et al., "Purification and Characterization of Phosphatidylethanolamine N–Methyltransferase from *Zymomonas mobilis*", Agric. Biol. Chem., 1987, 51(5), pp. 1425–1430.

M. Rohmer et al., "Bacterial Sterol Surrogates, Biosynthesis of the Side–chane of Bacteriohopanetetrol and of a Carbocyclic Pseudopentose from $^{13}$C–Labelled Glucose in *Zymomonas mobilis*", J. Chem. Soc., Chem. Commun., 1989, pp. 1471–1472.

RECOMBINANT CELLS THAT HIGHLY EXPRESS CHROMOSOMALLY-INTEGRATED HETEROLOGOUS GENES

This application is a continuation-in-part of application Ser. No. 08/013,658 (filed Feb. 4, 1993), now abandoned, which is a continuation of application Ser. No. 07/624,227 (filed Dec. 7, 1990), now abandoned, which is a continuation-in-part of application Ser. No. 07/352,062 (filed May 15, 1989), issued as U.S. Pat. No. 5,000,000, which is a continuation-in-part of application Ser. No. 07/239,099, (filed Aug. 31, 1988) now abandoned.

Work relating to this invention was supported in part by Grant FG05-86ER3574 from the Office of Basic Energy Science, U.S. Department of Energy, and in part by Grant 88-37233-3987 from the Alcohol Fuels Program, U.S. Department of Agriculture. The U.S. Government has certain rights in the invention.

BACKGROUND OF THE INVENTION

The present invention relates to recombinant host cells that comprise a heterologous, polypeptide-encoding polynucleotide segment which is stably integrated into a chromosome and which is under control of an endogenous promoter. When the integrated segment comprises, for example, ethanol-production genes from an efficient ethanol producer like *Zymomonas mobilis,* recombinant *Escherichia coli* and other enterobacterial cells within the present invention are capable of converting a wide range of biomass-derived sugars efficiently to ethanol. This invention also relates to mutations that enhance production of proteins encoded by chromosomally-integrated, heterologous genes which are expressed under the control of an endogenous promoter, and to methods of identifying such mutations.

During glycolysis, cells convert simple sugars, such as glucose, into pyruvic acid, with a net production of ATP and NADH. In the absence of a functioning electron transport system for oxidative phosphorylation, at least 95% of the pyruvic acid is consumed in short pathways which regenerate $NAD^+$, an obligate requirement for continued glycolysis and ATP production. The waste products of these $NAD^+$ regeneration systems are commonly referred to as fermentation products.

Microorganisms are particularly diverse in the array of fermentation products which are specific for each genus. See, for example, Krieg, N. R., and J. G. Holt, eds. [1984] BERGEY'S MANUAL OF SYSTEMATIC BACTERIOLOGY (Williams & Wilkins Co., Baltimore). These products include organic acids, such as lactate, acetate, succinate, and butyrate, as well as neutral products like ethanol, butanol, acetone, and butanediol. Indeed, the diversity of fermentation products from bacteria has led to their use as a primary determinant in taxonomy. Krieg and Holt [1984], supra.

End products of fermentation share several fundamental features. They are relatively nontoxic under the conditions in which they are initially produced but become more toxic upon accumulation. They are more reduced than pyruvate because their immediate precursors have served as terminal electron acceptors during glycolysis. The microbial production of these fermentation products forms the basis for our traditional and most economically successful applications of biotechnology and includes dairy products, meats, beverages, and fuels.

Most fuel ethanol is currently produced from hexose sugars in corn starch or cane syrup utilizing either *Saccharomyces cerevisiae* or *Zymomonas mobilis* (*Z. mobilis*). However, these are relatively expensive sources of biomass sugars and have competing value as foods. In addition, during fermentation much of the hexose is necessarily converted back to biomass, comprising microbial cells, rather than to ethanol. For conventional ethanol-producing microorganisms, this biomass has limited commercial value at best, for instance, as a nutritional supplement, and therefore, represents inefficient utilization of the expensive sugar substrate.

Starches and hexose sugars represent only a fraction of the total carbohydrates in plants. The dominant forms of plant carbohydrate in stems, leaves, hulls, husks, cobs, etc., are the structural wall polymers, cellulose and hemicellulose. Hydrolysis of these polymers releases a mixture of neutral sugars which include glucose, xylose, mannose, galactose, and arabinose. No known organism in nature can rapidly and efficiently metabolize all of these sugars, particularly the pentoses, into ethanol or any other single product of value.

*Escherichia coli* (*E. coli*) and related enteric bacteria are the main commercially useful microorganisms that are capable of metabolizing the entire range of biomass-derived sugars by fermentation under anaerobic conditions. However, under anaerobic fermentation conditions, these organisms convert sugars to a mixture of soluble products, including small amounts of ethanol, that cannot be separated economically. See Ingram, L. O., T. Conway, D. P. Clark, G. W. Sewell, and J. F. Preston [1987] *Appl. Environ. Microbiol.* 53:2420–2425. Thus, such enteric bacteria efficiently utilize the entire range of biomass-derived sugars but fail to produce a product of sufficient yield and uniformity to be commercially valuable.

Accordingly, there is a need for microorganisms which combine the efficient metabolism of the entire range of biomass-derived sugars, which is exhibited by certain enteric bacteria, such as *E. coli,* with the ability to produce high levels of a single, predominant, soluble fermentation product of commercial value, such as ethanol. Further, there is a continuing need for such organisms that can produce microbial biomass comprising additional products, such as commercially valuable proteins, in sufficient yield and quality for economical recovery.

Fermentation pathways transform pyruvic acid into a mixture of acidic and neutral products. Two pathways dominate in enteric bacteria such as *E. coli.* Lactate dehydrogenase catalyzes the reduction of pyruvate to lactic acid, directly oxidizing NADH to $NAD^+$. The second pathway, involving pyruvate formate-lyase, is more complicated. Pyruvate formate-lyase, which catalyzes the cleavage of pyruvate to formate plus acetyl-coenzyme A, is a central enzyme of the anaerobic metabolism of *E. coli,* because under anaerobiosis this enzyme is responsible for metabolizing a large fraction of pyruvate. The *E. coli* gene encoding pyruvate formate-lyase (pfl gene) has been cloned and sequenced. See Christiansen, L., and S. Pedersen [1981] *Mol. Gen. Genet.* 181:548–551; Rodel, W., W. Plaga, R. Frank, and J. Knappe [1988] *Eur. J. Biochem.* 177:153–158. The pfl gene is preceded by multiple promoters, and it is induced to high levels of expression by anaerobiosis. See Sawers, G., and A. Bock [1988] *J. Bacteriol.* 170:5330–5336.

The DNA used to provide ethanol-production genes for a recombinant host of the subject invention is isolated, for example, from *Z. mobilis.* This is a microorganism with unusual metabolic characteristics which is commonly found in plant saps and in honey. Wild-type *Z. mobilis* has long served as a natural inoculum for the fermentation of the Agave sap to produce pulque, a Mexican alcoholic beverage, and as an inoculum for palm wines. As noted above, this organism is also used for fuel ethanol production and has been reported to be capable of ethanol production rates which are substantially higher than those of yeasts.

Although Z. mobilis is nutritionally simple and capable of synthesizing amino acids, nucleotides and vitamins, the range of sugars metabolized by this organism is very limited and normally consists of glucose, fructose and sucrose. Substrate level phosphorylation from the fermentation of these sugars is the sole source of energy for biosynthesis and homeostasis. Z. mobilis is incapable of growth without a fermentable sugar even in rich medium such as nutrient broth.

In Z. mobilis, two enzymes, pyruvate decarboxylase (PDC) and alcohol dehydrogenase, particularly form II (ADHII), are required to convert pyruvate to ethanol and regenerate $NAD^+$. High levels of the individual proteins are found in the cytoplasm of Z. mobilis, ranging from 2% to 5% each of the soluble protein. Such high levels are presumed to be essential for the high rates of NADH oxidation and glycolytic flux required for energy production. The cloning and sequencing of Z. mobilis pdc and adhB genes encoding PDC and ADHII, has been previously reported. See Conway, T., Y. A. Osman, J. I. Konnan, E. M. Hoffman, and L. O. Ingram [1987] *J. Bacteriol.* 169:949–954; Conway, T., G. W. Sewell, Y. A. Osman, and L. O. Ingram [1987] *J. Bacteriol.* 169:2591–2597; Brau, B., and H. Sahm [1986] *Arch. Microbiol.* 146: 105–110; Brau, B., and H. Sahm [1986] *Arch. Microbiol.* 144:296–301; Neale, A. D., R. K. Scopes, R. E. H. Wettenhall, and N. J. Hoogenraad [1987] *Nucleic Acid. Res.* 15:1753–1761; Ingram, L. O., and T. Conway (1988] *Appl. Environ. Microbiol.* 54:397–404; Ingram, L. O, T. Conway, D. P. Clark, G. W. Sewell, and J. F. Preston [1987] *Appl. Environ. Microbiol.* 53:2420–2425.

Molecular genetics offers the potential to combine in a single organism the pathway for anaerobic metabolism in pentose-utilizing enteric bacteria, such as *E. coli*, and the efficient pathway for ethanol production from an ethanol producer such as Z. mobilis. Thus, expression of the Z. mobilis pdc gene in enteric bacteria such as *E. coli, Erwinia chrysanthemi* and *Klebsiella planticol* partially diverts the flow of pyruvate to ethanol as a fermentation product by using low levels of native ADH activity. More efficient ethanol production and higher concentrations of ethanol have been obtained with recombinant *E. coli* harboring the Z. mobilis genes encoding PDC and ADHII on a multi-copy plasmid. See Ingram et al. [1987], supra; Neale, A. D., R. K. Scopes, and J. M. Kelly [1988] *Appl. Microbiol. Biotechnol.* 29: 162–167. *E. coli* B (pLOI297) and *E. coli* ATCC 15224 (pLOI297) strains-are superior constructs in terms of ethanol production and environmental hardiness. See Alterthum, F., and L. O. Ingram [1989] *Appl. Environ. Microbiol.* 55:1943–1948. These recombinant *E. coli* efficiently ferment glucose, lactose, and xylose to ethanol.

The recombinant *E. coli* described above achieved useful levels of ethanol production using plasmid-borne ethanol-production genes from, Z. mobilis. Further, initial testing of ethanol production in prototype strains was facilitated by placing the exogenous genes on a multi-copy plasmid. However, the exogenous genes were not completely stable because of the inherent instability of plasmids in the absence of selective pressure to ensure their retention in the host cell. Due to plasmid incompatibilities, moreover, the use of a typical *E. coli* expression plasmid for the ethanol-production genes precludes the most convenient means for introduction into a basic commercial ethanol-producer strain of additional exogenous genes for production of other selected products, such as valuable proteins.

SUMMARY OF THE INVENTION

The present invention pertains to recombinant host cells that express chromosomally-integrated heterologous genes encoding useful polypeptides at high levels. According to one aspect of the present invention, such recombinant cells are obtained by first inserting a heterologous DNA segment encoding the desired polypeptide(s) into a host cell chromosome under the control of an endogenous promoter which is preferably a strong promoter. Optionally, the transformed cells are then treated with a mutagen. Finally, transformants are tested for expression of heterologous genes, either by genetic selection or screening, to find those having a mutation that causes increased expression of the inserted DNA segment resulting in an increase in production of each polypeptide encoded by the inserted DNA segment.

The chromosomally-integrated, heterologous genes and the mutation that effects increased expression are extremely stable even in the absence of conditions that select for retention of increased gene expression. Also, the engineered hosts are environmentally safer than conventional, plasmid-based recombinant production systems because they do not carry mobile genetic elements.

Specifically exemplified is a recombinant enteric bacterium, *Escherichia coli*, that is capable of efficiently converting the entire range of biomass-derived sugars to ethanol using exogenous ethanol-production genes from an efficient ethanol producer, such as *Zymomonas mobilis*. These ethanol genes are stably integrated into the chromosome of the recombinant host under the control of an endogenous promoter for an *E. coli* pyruvate formate-lyase (pfl) gene. The chromosome of this host further comprises a mutation that increases production of the ethanol-production proteins according to this invention. These recombinant hosts can accommodate the usual *E. coli* expression plasmids for efficient co-production with ethanol of other desirable products, such as commercially valuable proteins. Accordingly, the residual biomass from high volume fermentation of the bacteria of this invention to produce ethanol may optionally provide one or more additional high-value products in great abundance.

A further example is provided by recombinant *Klebsiella oxytoca* which also carries ethanol-producing genes from Z. mobilis stably integrated into the host chromosome. This bacterium is capable of efficiently producing ethanol from cellobiose and cellotriose, as well as from monomeric sugars.

More particularly, one aspect of the present invention relates to a recombinant host cell comprising a chromosome comprised of (a) a heterologous DNA segment under transcriptional control of a promoter endogenous to that host cell, where the DNA segment encodes a desired polypeptide; and (b) a mutation that causes increased expression of the heterologous DNA segment resulting in an increased production by the recombinant host cell of the desired polypeptide, compared to production of that polypeptide by the recombinant cell in the absence of the mutation. This increased expression of the heterologous DNA segment is retained in the absence of conditions that select for cells having such increased expression. In one preferred embodiment the chromosome of the recombinant host cell comprises a heterologous DNA segment that encodes a plurality of genes. Advantageously, among the plurality of genes is a selectable marker gene.

The present invention also relates to a cell strain that is the product of a process comprising the steps of (a) providing a culture comprised of host cells comprising a chromosome that encodes a promoter endogenous to these host cells and a host gene for integration of heterologous genes that is under transcriptional control of the endogenous promoter;

(b) transforming host cells in this culture with a heterologous DNA segment comprising
  (i) a plurality of genes including a selectable marker gene and a gene encoding a desired polypeptide, and
  (ii) sequences that are sufficiently homologous to the host gene and properly located in the heterologous DNA segment to enable integration into the host gene of the plurality of genes encoded by the heterologous DNA segment by means of homologous recombination;

(c) selecting for host cells in the above culture, or progeny thereof, that express the selectable marker gene at a first level;

(d) screening host cells selected in step (c), or progeny thereof, to obtain host cells that produce the desired polypeptide at an initial level;

(e) optionally exposing the host cells identified in step (d), or progeny thereof, to a mutagen under conditions such that mutations are created in the host cell chromosome; and then (f) testing host cells produced in step (d) or step (e), or progeny thereof, for host cells that produce the desired protein at a level higher than the initial level, to obtain bacteria having a mutation that causes increased expression of the heterologous DNA segment.

This increased expression results in an increase in production by the host cells of the desired polypeptide compared to production of desired polypeptide by these host cells in the absence of the mutation. Furthermore, enhanced expression of the integrated heterologous DNA is retained in the absence of conditions that select for cells having such increased expression.

In preferred embodiments of the present invention, the above-described process is further qualified as follows:

(i) In step (b), the heterologous DNA segment further comprises a plasmid which comprises a replicon that is temperature-sensitive for replication.

(ii) In step (b), the process of transforming host cells also comprises introducing the heterologous DNA segment into host cells and growing these host cells under conditions that select for cells that express the selectable marker gene at the first level. The cells are grown at a temperature that does not permit replication of the plasmid, resulting in integration of the heterologous DNA segment into the host gene of the chromosome by a homologous recombination event.

(iii) In step (c), the process of selecting for host cells further comprises growing the host cells that express the selectable marker gene at the first level under conditions that do not select for cells that express the selectable marker gene. In particular, these host cells are grown under these nonselective conditions at a first temperature that does permit replication of the plasmid, resulting in spontaneous excision from the host gene of the plasmid and the selectable marker gene by a second homologous recombination event. The host cells are then grown under the nonselective conditions at a second temperature that does not permit replication of the plasmid, resulting in host cells that retain the gene encoding the desired polypeptide in the absence of the selectable marker gene and the plasmid.

The basis of using nonselective conditions and a nonpermissive temperature for plasmid replication to obtain according to this aspect of the invention is that integration of the plasmid replicon into the chromosome provides a slight inhibition of growth rate. Therefore, strains which have excised plasmid grow slightly faster than those retaining integrated plasmid, thus providing the basis for enrichment of clones which have deleted the plasmid replicon and, coincidentally, the selectable marker gene.

In another preferred embodiment relating to this aspect of the invention, the above-described process is further qualified such that (i) in step (b) the heterologous DNA segment comprises a closed circular DNA lacking an ability to replicate and (ii) in step (f) the process of testing host cells comprises selecting for host cells produced in step (d) or step (e), or progeny thereof, that express the selectable marker gene at a second level that is higher than the first level, and then screening these host cells that express the selectable marker gene at the second level for host cells that produce the desired protein at a level higher than the initial level. When the selectable marker gene confers resistance to chloramphenicol, for example, host cells produced in step (d) or (e) of the above process may express the chloramphenicol resistance gene at a first level that confers resistance to at least about 20 $\mu$g/ml of chloramphenicol. In those embodiments where the process involves further selection for cells carrying mutations that cause a second, higher level of expression of the chloramphenicol resistance gene, the second level of expression may confer resistance to at least about 100 $\mu$g/ml of chloramphenicol. Advantageously, selection for mutant cells with a higher level of expression of chloramphenicol resistance may be carried out using about 600 $\mu$g/ml of chloramphenicol.

A recombinant host cell of this invention can be a microbial cell, such as an enteric bacterium. Illustrative of suitable enteric bacteria in this regard are strains of *Erwinia chrysanthemi, Escherichia coli, Klebsiella pneumoniae,* and *Klebsiella oxytoca.*

The heterologous DNA segment which is chromosomally integrated into the genome of the recombinant host, in accordance with the present invention, is preferably under the control of a strong endogenous promoter, for example, the pyruvate formate-lyase (pfl) promoter.

In certain embodiments, the heterologous DNA segment encodes an alcohol dehydrogenase and a pyruvate decarboxylase from an organism that produces high levels of ethanol. Such enzymes are exemplified by an alcohol dehydrogenase and a pyruvate decarboxylase encoded by genes from *Zymomonas mobilis.* In a preferred embodiment of the present invention, the recombinant host cell is able to produce ethanol by fermentation, for example, of glucose or xylose, with theoretical yields corresponding to conversion of at least about 90% or 100%, respectively, of added sugar to ethanol. In some cases the observed yields of ethanol appear to exceed those possible based on the amount of added sugar, a result reflecting co-catabolism of complex nutrients to pyruvate and thus to ethanol.

In accordance with an additional aspect of the present invention, a recombinant host cell as described above is provided that contains a chromosome comprising a further mutation, particularly a mutation in a fumarate reductase (frd) gene, that impairs succinate production, reducing production of acid which can inhibit ethanol production.

A recombinant host cell within the present invention optionally may comprise a further mutation that impairs recombination in the cell, to make the cell safer environmentally by reducing its ability to interact with mobile genetic elements. In one embodiment, the mutation that impairs recombination comprises a mutation in a recA gene.

A recombinant host cell of this invention can be produced by various processes in addition to those particularly exemplified here. Exemplary of such processes are genetic-engineering methods for insertion of a heterologous DNA segment into a predetermined location on a host cell chromosome, and for generation and identification of mutations which enhance expression. In particular, standard molecular genetic analyses of a recombinant microbial strain of the present invention will enable one to employ other methods to make recombinant host cells which likewise fall within the present invention. For example, knowledge of the DNA-sequence changes associated with a particular mutation effected in accordance with the present invention enables the design, synthesis and insertion into a host chromosome of a heterologous DNA segment containing not only genes coding for desired proteins but also a promoter and a mutation effecting high-level expression of the genes. Such a genetic construct, comprising a heterologous DNA segment that includes an appropriate mutation and promoter with the desired genes, is therefore another embodiment within the present invention.

BRIEF DESCRIPTION OF THE DRAWINGS

FIG. 5 illustrates the ethanol production from glucose (100 g/liter) by: (●) strain M5A1(pLOI555), (▲) strain P2 containing integrated PET genes O, M5A1 control, (■) strain EL containing integrated PET genes. FIG. 6 illustrates the ethanol production from cellobiose (100 g/liter) fermentation by strain P2. (▲), ethanol; (Δ), cell mass.

DETAILED DESCRIPTION OF PREFERRED EMBODIMENTS

Figure 1:
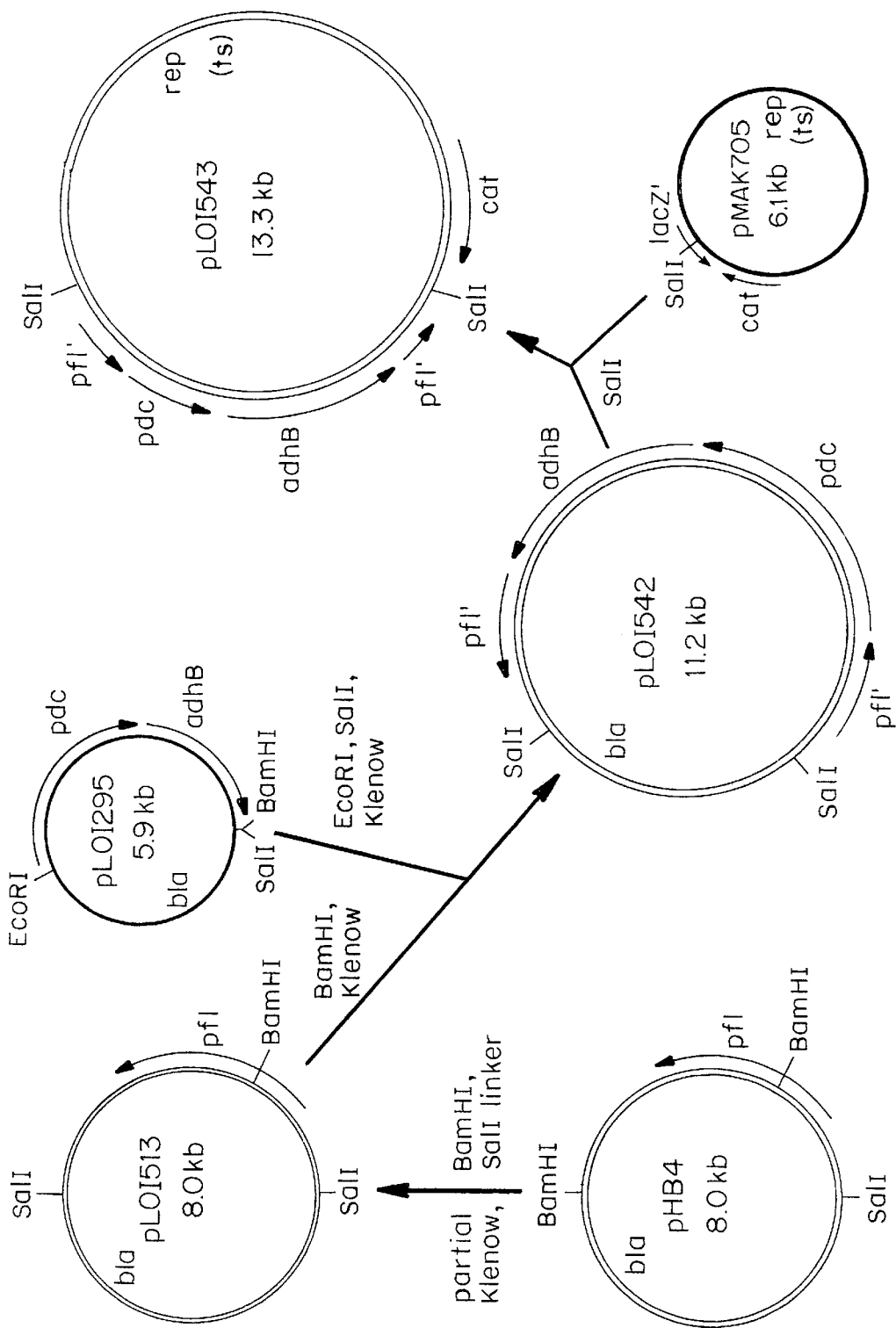
FIG. 1 is a schematic diagram illustrating construction of an integration vector (pLOI543), containing a temperature-conditional replicon (pSC101; Hamilton, C. M., M. Aldea, B. K. Washburn, P. Babitzke, and S. R. Kushner [1989] *J. Bacteriol.* 171:4617–22) for the integration of ethanol-production genes (Z. mobilis pdc and adhB genes) and a chloramphenicol resistance gene into a pfl gene of an *E. coli* chromosome. Abbreviation: Klenow, convert to blunt by filling bases in overhang region using the Klenow fragment of *E. coli* DNA polymerase I.

The present invention relates to a recombinant host cell comprising a chromosome comprised of (a) a heterologous DNA segment under transcriptional control of a promoter endogenous to that microbial cell, where the DNA segment encodes a desired polypeptide; and (b) a mutation that causes increased expression of the heterologous DNA segment resulting in an increase in production by the host cell of the desired polypeptide compared to production of that polypeptide by the host cell in the absence of this mutation. Enhanced expression of the heterologous DNA segment is retained in the absence of conditions that select for cells having such increased expression.

Definitions: In the present context, "heterologous" DNA segment means that the DNA segment contains a sequence that is different from the sequence in the corresponding position downstream from the endogenous promoter in the chromosome of the cell into which the heterologous segment has been inserted. Thus, the heterologous DNA segment of the present invention includes a DNA segment taken from one location in a host chromosome and inserted into another location (under control of an endogenous promoter other than the one naturally associated with that segment), as well as a DNA segment from another organism. The nucleotide sequence of the heterologous DNA segment encodes one or more structural genes and is derived from any genetic source, including, for example, eukaryotic or prokaryotic cellular or viral genomes, or from artificial coding sequences created by genetic engineering.

The heterologous segment is under the transcriptional control of an endogenous promoter by virtue of being integrated into a host cell chromosome on the downstream (3') side of the promoter. As previously noted, the endogenous promoter is preferably a "strong" promoter, in the sense that it provides a high level of gene expression in relation to a more typical microbial promoter, such as the lactose operon (lac) promoter of *E. coli*. Among strong promoters are those that include a single site for promoter activity, i.e., for binding RNA polymerase and directing the enzyme to the correct transcriptional start site, and those that include a plurality of such sites. Illustrative of the former (single-site) category of strong promoters is the well-known tryptophan (trp) promoter. The latter (multi-site) category is exemplified by the promoter for a pyruvate formate-lyase (pfl) gene, homologous variants of which are found in *E. coli* and other enteric bacteria. Pyruvate formate-lyase is normally expressed at a high level, particularly under the anaerobic conditions which pertain during fermentation without forced aeration. The pfl promoter in fact includes seven sites for promoter activity, as reflected, for example, in sequence analyses of the pfl mRNA and in "footprinting" data indicating where RNA polymerase is bound, or in "primer extension" analyses indicating the 5' end of a mRNA.

In this description, "mutation" denotes a relatively permanent change in hereditary material, typically involving a biochemical change in the codons that make up genes but also possibly involving a physical change in chromosome relations. A mutation suitably employed according to the present invention causes increased expression of the heterologous DNA segment, resulting in enhanced production by the host cell of each polypeptide encoded by that segment, relative to production of each polypeptide by the host cell in the absence of the mutation. The increased expression thus achieved is retained in the absence of conditions that select for cells having such increased expression. For example, in bacterial strains having mutations, according to the present invention, that increase expression of both antibiotic resistance and ethanol-production enzymes integrated into a chromosome, no loss of high-level expression of the integrated genes is detectable after as many as 68 population doublings, even without selection with antibiotic.

Transformed host cells bearing a mutation according to the present invention may be detected conveniently by means of the increased expression of one or more polypeptides encoded by the inserted DNA segment, according to standard genetic methodology. Increased expression of a polypeptide may be determined by direct detection of a polypeptide or inferred from an activity attributable to that polypeptide. Advantageously, one of the genes encoded by the inserted DNA segment can be a selectable marker gene, for example, a gene which confers antibiotic resistance to the host. In this case, mutant cells with increased expression of the antibiotic resistance gene may be selected conveniently using antibiotic concentrations above a first level that inhibits host cells lacking a mutation that increases expression of the heterologous DNA segment.

More particularly, it has been discovered that mutations suitable for use in the present invention can be obtained reliably as spontaneous mutants or by induction via conventional mutagenesis, followed by selection or by screening for cells having the desired phenotype of high-level expression of integrated genes. Thus, suitable mutations in certain bacteria are found to arise spontaneously at a frequency on the order of $10^{-4}$ to $10^{-5}$, upon selection for cells having increased expression of an integrated chloramphenicol resistance gene, such that cell growth occurs at a concentration of antibiotic 30 times higher than that tolerated in the absence of such a mutation. Similarly, after treatment of certain bacterial cells with a mutagen, suitable mutations can be obtained at a frequency of about 0.5– $1 \times 10^{-4}$ of the survivors of mutagenesis by screening for cells having expression of ethanol-related enzymes at. levels about ten times higher than in the absence of such mutagenic treatments.

Mutations suitable for use in the present invention actually cause overexpression of inserted genes to the extent that polypeptide production from a single copy of a gene chromosomally inserted, according to this invention, is comparable to production achieved with multiple copies of the same gene carried on a multi-copy plasmid. For example, bacterial cells carrying such a suitable mutation can express integrated genes, say, for chloramphenicol resistance and ethanol production, at levels that are functionally equivalent to a cell containing 30 to 300 copies of the same genes on a multi-copy plasmid.

A molecular basis has not been determined for mutations identified, as described herein, for use according to the present invention. Nevertheless, the magnitude of the increase in gene expression (on the order of about ten fold, for example) that is obtained in a single screening or selection step is substantially greater than that expected for a mutation mechanism involving gene duplication. To achieve a comparable increase in selectable gene expression by means of gene duplication typically requires repeated selection steps with progressively higher levels of selective agent. Moreover, the low (in fact, undetectable) frequency of reversion of the present mutations also militates against gene duplication as a basis for these mutations. In fact, it is known that mutations which produce increased gene expression by means of tandem gene repetition are typically unstable and cannot be retained in the absence of conditions that select for cells having such increased gene expression, in contrast to mutations of the present invention. Conversely, the observed frequency of suitable mutations arising spontaneously, according to the present invention, is compatible with a causal mechanism involving point mutations.

Selection of mutations that enhance expression of integrated genes using a selectable marker gene may be performed pursuant to the present invention in any type of host cell for which practical genetic methods are known in the art for selecting clones having mutations that are inducible at a frequency on the order of at least about $10^{-4}$ per survivor of mutagenic treatment. Similarly, screening for mutant host cells pursuant to the present invention requires practical methods for preparation of sufficient numbers of clones, each comprising enough cells for detection of high-level expression of a desired integrated gene by a method appropriate to the particular desired gene.

Such selection or screening for suitable mutations is most easily effected with host cells which are readily culturable in large quantities, as in the case of prokaryotic (bacterial) and yeast cells. For purposes of this description, such a host is denoted a "microbial cell," and the strain it comprised is a "microbial strain." Under this rubric of microbial cells, enteric bacteria like *Erwinia chrysanthemi, Escherichia coli* and *Klebsiella planticola* are particularly attractive hosts because they are capable of utilizing a wide variety of sugars, including pentoses and lactose. While microbial cells are preferred hosts, the present invention also contemplates the use of other types of cellular hosts, including fungal cells and eukaryotic (animal, insect and plant) cells, into which a heterologous DNA segment can be inserted under control of an endogenous promoter. Thus, the host cell need only be amenable to a selection or screening regimen for cells having increased expression of the integrated heterologous DNA, as described above, thereby to obtain suitable enhanced-expression mutants.

Embodiment relating to ethanologenic *E. coli:* An illustrative application of the present invention involves the integration of *Z. mobilis* genes for ethanol production into the pfl region of an *E. coli* chromosome. The pfl gene is central to normal fermentative metabolism, catalyzing the conversion of pyruvate to formate plus acetyl-CoA and providing an essential source of acetyl units for biosynthesis. Insertional inactivation of this gene thus represents inhibition of a competing branch point for the diversion of pyruvate away from production of ethanol by the microorganism. Additional genetic improvements are also described which eliminate succinate production and inactivate the recA gene.

These recombinant bacteria are useful for the manufacture of recombinant polypeptides as co-products during ethanologenic fermentation of biomass sugars. As a result of integration into the chromosome, the stability of the ethanol production trait is improved significantly compared to comparable plasmid-based systems for the purposes of industrial-scale fermentation to produce ethanol: 100% retention of the ethanol genes after 68 generations compared to only 97% with a comparable plasmid-based construct.

Also, elimination of the plasmid carrying ethanol-production genes allows insertion of plasmids for producing co-products without interference with the ethanol production ability.

Biological deposits: The following cultures have been deposited with the American Type Culture Collection (ATCC), 12301 Parklawn Drive, Rockville, Md., 20852, USA. Table 1 lists the accession numbers assigned to the cultures by the repository.

TABLE 1

Biological deposits

| Culture | Accession Number |
|---|---|
| E. coli (pLOI510) | ATCC 68484 |
| E. coli (pLOI543) | ATCC 68485 |
| E. coli KO4 | ATCC 55123 |
| E. coli KO11 | ATCC 55124 |
| E. coli KO12 | ATCC 55425 |
| E. coli KO20 | ATCC 55126 |

The subject cultures have been deposited under conditions that assure that access to the cultures will be available during the pendency of this patent application to one determined by the Commissioner of Patents and Trademarks to be entitled thereto under 37 CFR §1.14 and 35 USC §122. The deposits are available as required by foreign patent laws in countries wherein counterparts of the subject application, or its progeny, are filed. It should be understood, however, that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit(s), and in any case, for a period of at least 30 (thirty) years after the date of deposit or for the enforceable life of any patent which may issue disclosing the cultures. The depositor acknowledges the duty to replace the deposits, should the depository be unable to furnish a sample when requested, due to the condition of the deposit. All restrictions on the availability to the public of the subject culture deposits will be irrevocably removed upon the granting of a patent disclosing them.

Integration of Z. mobilis pdc and adhB genes into the E. coli B chromosome: Two approaches embodied in examples set out below represent different strategies which can be employed, in accordance with the present invention, to construct a bacterial strain, such as E. coli (ATCC 11303), in which a foreign gene (here, the Z. mobilis genes for ethanol) is integrated into a chromosomal gene, illustrated by the pfl gene. The first approach entails the use of a derivative of the temperature-conditional integration vector developed by Hamilton et al. See Hamilton, C. M., M. Aldea, B. K. Washburn, P. Babitzke, and S. R. Kushner [1989] J. Bacteriol. 171:4617–22; and Example 3, infra.

Thus, as shown in the examples, ATCC 11303 was transformed with a temperature-dependent replication plasmid, pLOI543, followed by temperature-based selection and enrichment for two homologous recombination events, 64.5% of the colonies were sensitive to chloramphenicol (Cm), indicating loss of plasmid. Of these Cm-sensitive clones, 5.9% formed pink colonies on aldehyde test plates indicating the presence of Z. mobilis ADHII. Two of these clones having retained integrated ethanol-production genes but having lost the Cm-resistance gene and plasmid were selected for further study and designated KO1 and KO2.

Via a second approach, reflected in Example 4, a Cm-resistant transformant was obtained using the circularized SalI fragment from plasmid pLOI510 and was designated KO3. In this approach no replicating plasmid is introduced into the cell; only the ethanol-production genes and associated Cm-resistance gene are integrated into the chromosome. The KO3 clone also formed pink colonies identical to KO1 and KO2 on aldehyde indicator plates. Control ATCC 11303 formed white colonies (negative), while ATCC 11303 (pLOI297) carrying Z. mobilis ethanol genes on a plasmid formed intensely red colonies indicating a high level of Z. mobilis gene expression.

Subsequently, isolation of vector from these three recombinants was attempted by the alkaline SDS lysis method. No vector was visible in agarose gels of these preparations which had been stained with ethidium bromide. These preparations were also tested in transformation experiments with TC4 as the host with selection for Cm resistance. No transformants were recovered further confirming the absence of vector.

Figure 3A:
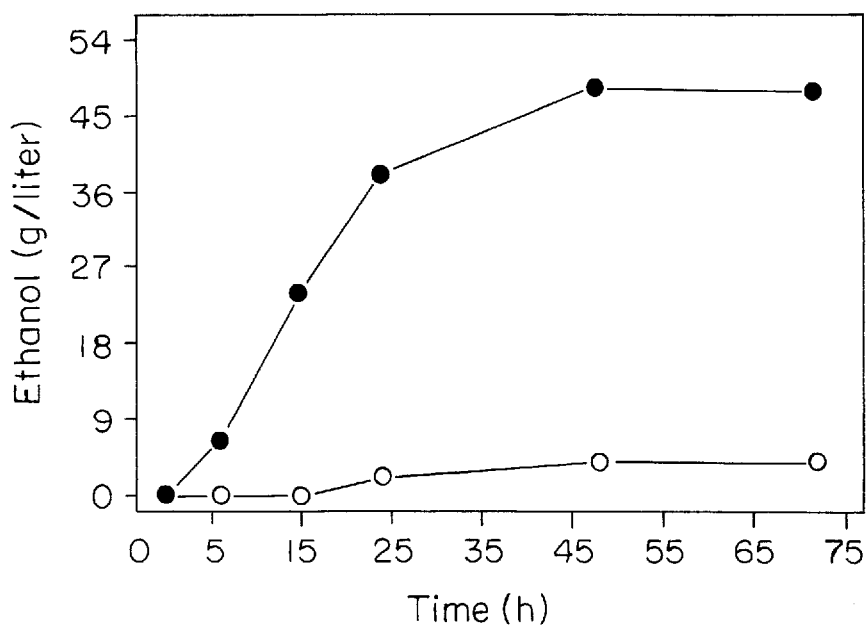
FIGS. 3A–G illustrates ethanol (A, C, E, G) production and growth (B, D, F) during batch fermentation. A and B. Fermentation of 10% glucose. Symbols: ●, plasmid-based ethanol production strain ATCC11303(pLOI297); ○, chromosomally-integrated ethanol production strain lacking an expression enhancing mutation, KO2. C. and D. Fermentation of 10% glucose. Symbols: ○, a chromosomally-integrated strain lacking a spontaneous expression enhancing mutation, KO3; ●, chromosomally-integrated strain containing a spontaneous expression enhancing mutation, KO4; ▲, KO4 supplemented with 22 mM sodium acetate. E. and F. Fermentation of 8% xylose. Symbols: ●, KO4; ▲, KO11, a further mutant of KO4, lacking fumarate reductase activity (frd); □, KO12, a further mutant of KO11, carrying a recA mutation. G. Fermentation by KO20, a chromosomally-integrated strain with an induced mutation. Symbols: ■, 10% glucose, ●, 8% xylose.
Figure 3B:
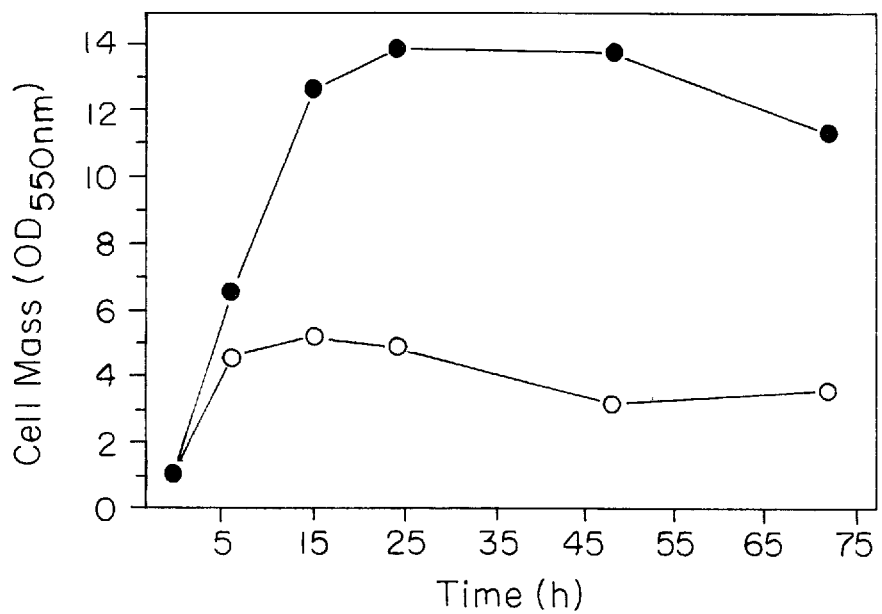

Fermentation by strains KO1, KO2, and KO3: FIG. 3A and B shows a comparison of fermentations by strains KO2 and ATCC 11303 (pLOI297) with 10% glucose. Fermentation by strain KO1 was identical to that by KO2 and is not presented. These new constructs were very inefficient producers of ethanol as indicated by the low volumetric productivity and ethanol yield (Table 2). Growth was limited to less than half that of ATCC 11303 (pLOI297) and only 4 g/liter of ethanol was produced after 72 hours. Although strain KO3 was slightly better than KO1 and KO2, it remained a very poor producer of ethanol (FIG. 3C–D; Table 2).

TABLE 2

Ethanol production from glucose and xylose by recombinant strains of E. coli (ATCC11303).

| | 10% Glucose | | | | | | | | | | | 8% Xylucose | | | |
|---|---|---|---|---|---|---|---|---|---|---|---|---|---|---|---|
| Parameter[a] | pLOI297[b] | KO1 | KO2 | KO3 | KO4 | KO5 | KO10 (recA) | KO11 (frd) | KO11 (frd)[D] | KO12 (frd, recA) | KO4 +Ac[e] | pLOI297[b] | KO4 (frd) | KO11 (frd, recA) | KO12 |
| Base (mmoles/ g sugar) | 1.1 | 5.7 | 6.3 | 5.5 | 1.3 | 1.4 | 1.1 | 0.6 | 0 | 1.1 | 1.0 | 1.4 | 1.6 | 0.5 | 0.64 |

TABLE 2-continued

Ethanol production from glucose and xylose by recombinant strains of E. coli (ATCC11303).

| | | | | 10% Glucose | | | | | | | | | 8% Xylucose | |
| --- | --- | --- | --- | --- | --- | --- | --- | --- | --- | --- | --- | --- | --- | --- |
| Parameter[a] | pLOI297[b] | KO1 | KO2 | KO3 | KO4 | KO5 | KO10 (recA) | KO11 (frd) | KO11 (frd)[D] | KO12 (frd, recA) | KO4 +Ac[e] | pLOI297[b] | KO4 (frd) | KO11 (frd, recA) | KO12 |
| Ethanol Yield (g/liter) | 48.8 | 4.0 | 4.0 | 10.4 | 52.8 | 52.8 | 51.2 | 52.8 | 38.8 | 54.4 | 54.4 | 36.0 | 36.0 | 41.6 | 40.8 |
| Ethanol Yield (g/g sugar) | 0.52 | 0.05 | 0.05 | 0.13 | 0.56 | 0.56 | 0.54 | 0.54 | 0.39 | 0.57 | 0.57 | 0.47 | 0.47 | 0.53 | 0.53 |
| Theoretical Yield (%) | 101 | 10 | 10 | 26 | 110 | 110 | 107 | 107 | 76 | 112 | 112 | 94 | 94 | 104 | 103 |
| Vol. Prod.[c] (g/liter*h) | 1.9 | 0.3 | 0.3 | 0.4 | 1.5 | 1.5 | 1.8 | 1.7 | 1.4 | 1.2 | 1.6 | 1.0 | 1.1 | 1.3 | 1.1 |
| 30-h Ethanol (g/liter) | 41.8 | 3.2 | 3.2 | 6.4 | 36.0 | 36.0 | 38.0 | 38.0 | 29.0 | 30.4 | 38.5 | 30.0 | 25.6 | 30.4 | 26.0 |
| Cell Yield (g/g sugar) | .048 | .021 | .021 | .028 | .044 | .040 | .041 | .042 | .041 | .035 | .045 | .050 | .047 | .051 | .048 |

[a]Calculations based on total sugar initially added.
[b]ATCC11303 (pLOI297) has plasmid-borne ethanol genes.
[c]Vol. Prod., volumetric Productivity = yield/time
[d]Fermentation conducted without pH control.
[e]Supplemented with 3 g/liter sodium acetate (22 mM final concentration).

Large volumes of base were consumed for maintenance of pH during fermentations by these three new strains, indicating excessive production of acidic fermentation, products.

Enhancement of expression of integrated pdc and adhB genes by mutations: The pink phenotype observed on aldehyde indicator plates appeared to indicate insufficient expression of Z. mobilis genes for ethanol production. A mutation that causes increased expression of the integrated genes in KO2 was obtained by screening for dark red phenotype on aldehyde indicator plates after mutagenesis with ethyl methane sulfonate under standard conditions well known in the art. Approximately 200 plates were analyzed with 200 to 400 colonies per plate. Four dark red clones were isolated, the increased color being indicative of increased expression of ADHII. One of these was designated strain KO20.

Selection for resistance to high levels of Cm was used to enrich for spontaneous mutants of KO3 to determine whether mutants expressing antibiotic resistance at a higher level also expressed the other inserted genes at a higher level. Serial dilutions of an overnight culture were plated on Luria agar plates containing 2% glucose and 600 μg/ml of Cm. Large raised colonies which are indicative of high-level expression of Z. mobilis pdc and adhBita genes were observed after overnight incubation at a frequency of approximately 1 per 100,000 plated cells. All of these colonies exhibited a dark red phenotype on aldehyde indicator plates identical to ATCC 11303 (pLOI297), the plasmid-based construct which is an excellent ethanol producing strain. Two mutants were retained for further study, strains KO4 and KO5. The lack of vector in these strains was again confirmed by the failure of DNA preparations from KO4 and KO5 to transform TC4 during selection for Cm resistance and by the absence of vector DNA in agarose gels stained with ethidium bromide.

Figure 3C:
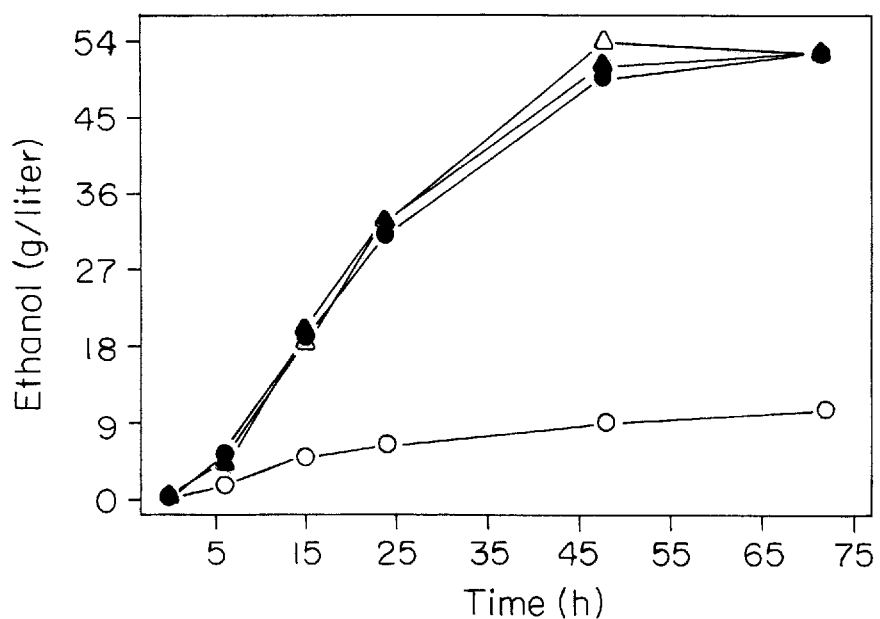
Figure 3D:
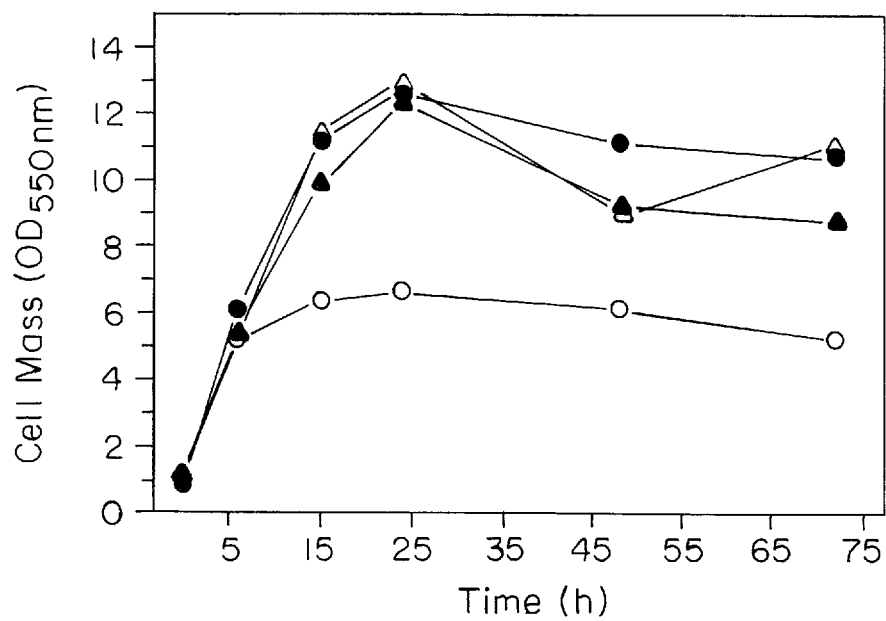

Fermentation by strains KO4, KO5 and KO20: FIG. 3C and D illustrate the fermentation of 10% glucose by KO4 and KO5, two strains in which spontaneous mutations that enhance expression of integrated ethanol-production genes were co-selected by selection for resistance to high levels of an antibiotic. Both strains were identical and only fermentation by KO4 has been plotted. Growth, cell yield, and ethanol yield by these improved constructs were almost equivalent to those of the plasmid-based construct, ATCC 11303 (pLOI297). See Table 2. Although the rate of ethanol production as indicated by volumetric productivities from the early stages and by the level of ethanol achieved after 30 hours was somewhat slower than ATCC 11303 (pLOI297), theoretical yields with KO4 and KO5 were higher and exceeded 100% based on added glucose. This higher yield during slower fermentation reflects co-catabolism of complex nutrients to pyruvate and thus to ethanol. These complex nutrients serve as the primary nitrogen source for biosynthesis. Continued denitrification caused an increase in the pH with KO4, KO5 and ATCC 11303 (pLOI297) after sugars were exhausted. The resulting rise in pH provides a convenient method to monitor sugar exhaustion.

Figure 3E:
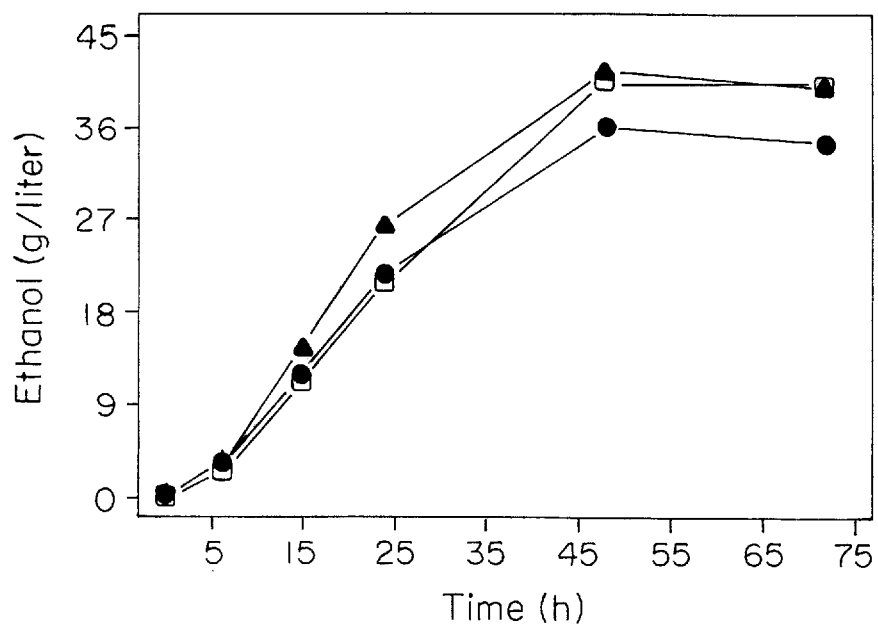
Figure 3F:
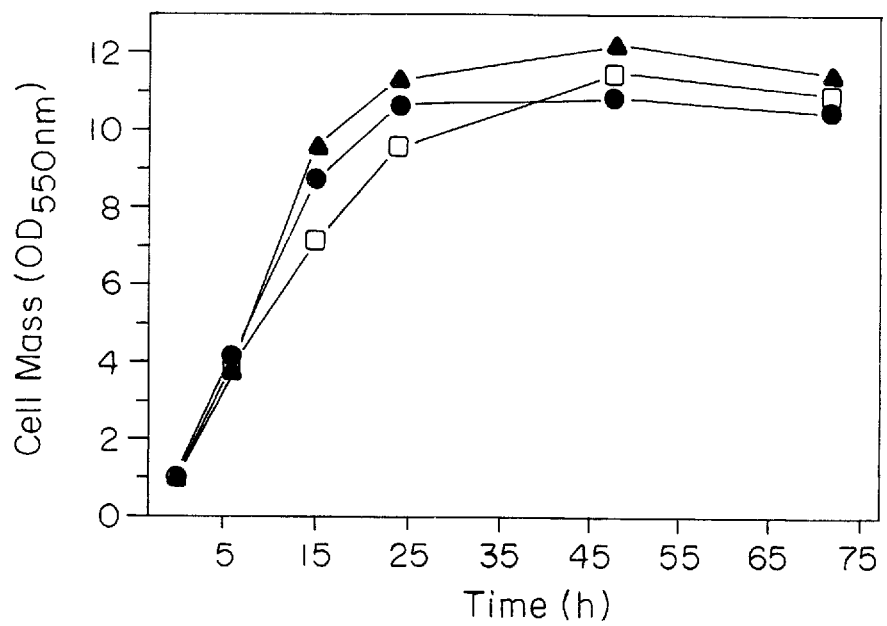

The fermentation of 8% xylose by strain KO4 and ATCC 11303 (pLOI297) were also compared (FIG. 3E and F). KO4 was equivalent to the plasmid-based strain in ethanol yield, although the rate of ethanol production was slightly slower as evidenced by the ethanol level after 30 hours (Table 2).

Figure 3G:
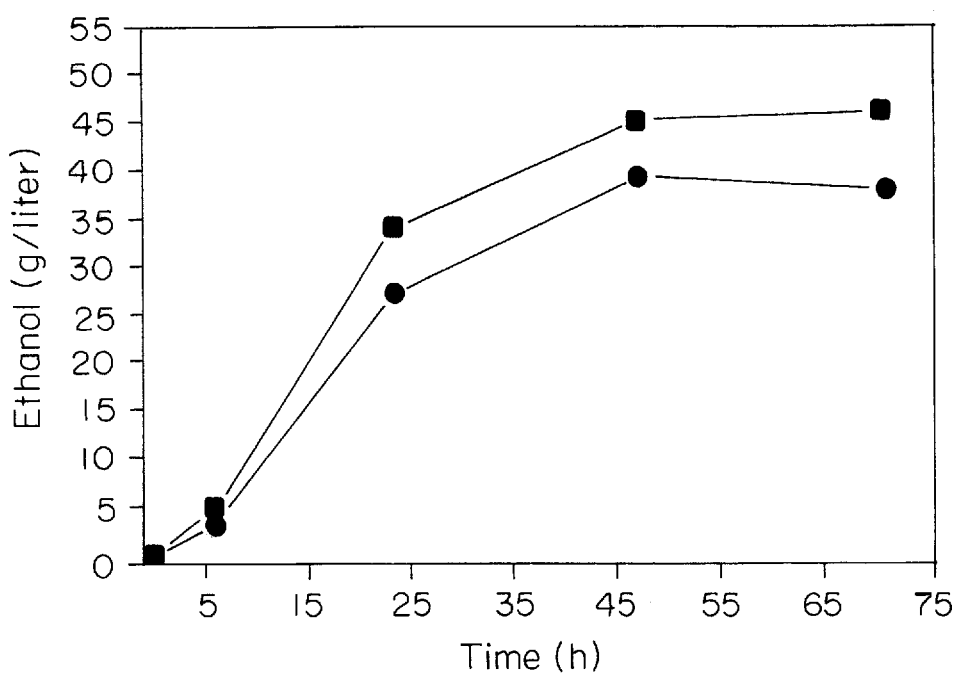

FIG. 3G illustrates the fermentation of 10% glucose and 8% xylose by strain KO20 which comprises an induced mutation that enhances expression of integrated ethanol-production genes. Fermentation of both sugars by this strain carrying an induced mutation was essentially the same as for strains KO4 and KO5 which carry spontaneous mutations selected by high levels of antibiotics.

Effect of added acetate: During anaerobic growth, the pfl gene product has been shown to be the primary route for acetate production and the primary source of acetyl-CoA for biosynthesis (7,17). Insertional inactivation by the Z. mobilis ethanol-pathway genes may lead to an acetate deficiency for lipid synthesis in derivatives of ATCC 11303. Supplementation with sodium acetate was found to improve the rate of ethanol production with a small increase in yield (FIG. 3C and D; Table 2).

Expression of Z. mobilis enxzymes in recombinant E. coli: The specific activity of Z. mobilis PDC was measured in French press extracts of selected recombinant strains.

PDC is a relatively thermostable enzyme and activities were measured in extracts after heat inactivation of native *E. coli* activities which complicate such measurements. No activity was detected in the control, strain ATCC 11303. Both KO2 and KO3 produced low levels of activity, 0.2 U/mg protein. Ten-fold higher activity was present in extracts of KO4 (2.1 U/mg protein), the high Cm-resistant mutant. The level of PDC in KO4 was almost equivalent to the level produced in the plasmid-based construct, ATCC 11303 (pLOI297), and similar to that found in native *Z. mobilis* (Ingram, L. O., and T. Conway (1988] *Appl. Environ. Microbiol.* 54:397–404).

Protein extracts from these strains were also examined by SDS-PAGE. Numerous changes in proteins were observed between ATCC 11303 and recombinant derivatives in addition those attributable to *Z. mobilis* genes. KO4 and ATCC 11303 (pLOI297) contained higher levels of a protein band in the 60,000 MW region corresponding to the size of PDC than were present in KO2 and KO3. This band was absent in the ATCC 11303 control. Many endogenous proteins were found in the 38,000 MW region where *Z. mobilis* ADHII would be found, obscuring differences in expression.

Organic acid production by *E. coli* ATCC11303 constructs: Considerable amounts of base were consumed by ethanologenic strains of *E. coli* during fermentations (Table 2) indicating the production of acids as co-products. As shown in Table 3, high levels of three acids are produced by the ATCC 11303 parent and by KO3. Although ATCC 11303 (pLOI297) and KO4 produced lower levels of acetic and lactic acids, succinate production by KO4 remained high. To eliminate succinate production, a frd mutation was introduced by insertion of a Tn10 vector using standard genetic methods, including selection for a tetracycline resistance marker of Tn10, followed by elimination of Tn10 using fusaric acid selection, resulting in an frd deletion due to imprecise excision of Tn10. The resulting strain (KO11) lacked fumarate reductase activity.

Figure 4A:
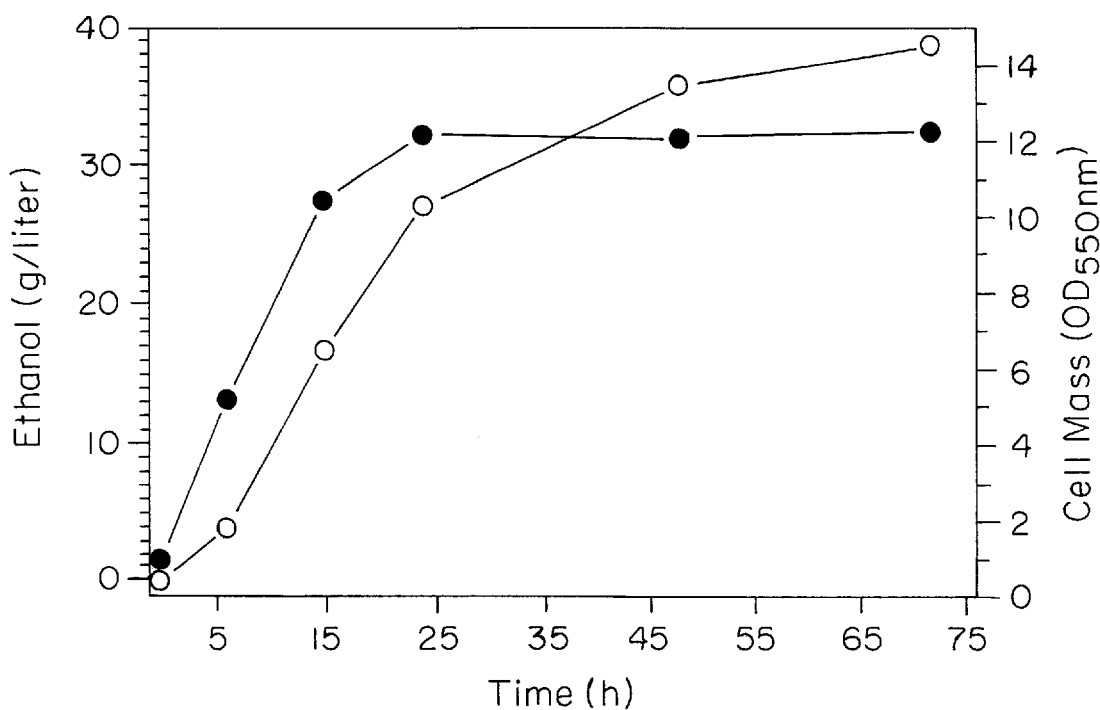
FIGS. 4A–B illustrates fermentation of 10% glucose by KO11 (frd) without pH control. A. Growth (●) and ethanol production (○). B. pH of broth (Δ).
Figure 4B:
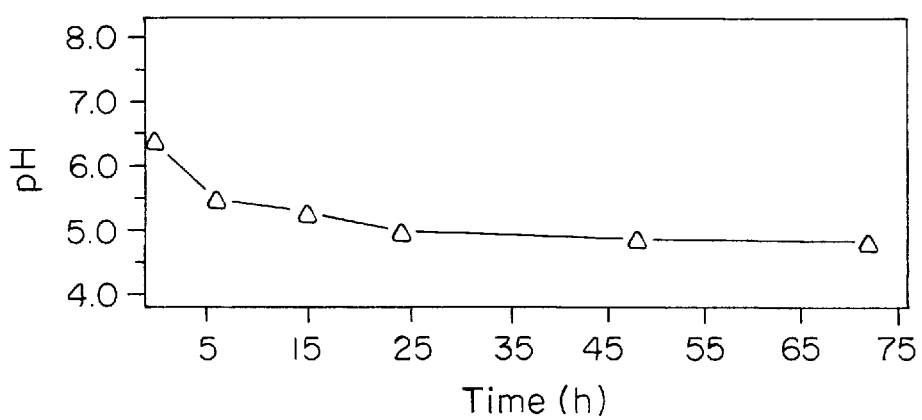

This frd mutation reduced the level of succinate produced during glucose fermentation to 3% that of the parent, KO4 (Table 3). However, without titration of acid during fermentation, this low level of acid production was still sufficient to reduce the pH of fermentations run without titration and, therefore, to reduce ethanol productivity from glucose (FIG. 4, Table 2).

However, with acid titration, the elimination of fumarate reductase did improve the rate of ethanol production, cell yield, and ethanol yield from xylose (Table 2). With titration, volumetric productivity from glucose was also increased by this mutation, although ethanol yield remained essentially the same (Table 2).

TABLE 3

Production of acidic fermentation products[a].

| Recombinant[b] | Organic Acid (mM) | | |
|---|---|---|---|
| | Acetic acid | Lactic acid | Succinic acid |
| ATCC11303 (None) | 66 | 641 | 58 |
| ATCC11303 (pLOI297) (plasmid-borne) | 21 | 32 | 49 |
| KO1 (integrated, no mutation) | 18 | 673 | 62 |
| KO2 (integrated, no mutation) | 18 | 602 | 57 |
| KO3 (integrated, spontaneous) | 69 | 525 | 66 |

TABLE 3-continued

Production of acidic fermentation products[a].

| Recombinant[b] | Organic Acid (mM) | | |
|---|---|---|---|
| | Acetic acid | Lactic acid | Succinic acid |
| KO4 (integrated, spontaneous) | 22 | 29 | 70 |
| KO10 (KO4, recA) | 18 | 20 | 73 |
| KO11 (KO4, frd) | 14 | 32 | 2 |
| KO12 (KO4, recA, frd) | 6 | 40 | 2 |
| KO20 (integrated, induced) | 4 | 60 | 2 |

[a]Average of two fermentations with 10% glucose, sampled after 72 h.
[b]Notes in parentheses indicate status of exogenous ethanol genes and related mutations that enhance ethanol production.

Comparison of the stability of chromosomally-integrated and plasmid-based genes in *E. coli*. ATCC 11303 (pLOI297), KO4 and KO5 were grown in the Luria broth containing 10% (w/v) glucose without antibiotic selection for up to 68 generations at 300C. Cultures were plated on selective and nonselective plates and on aldehyde indicator plates after 48 and 120 hours to determine the ratio of Cm-resistant CFU to total CFU as well as the proportion of ethanol-producing colonies. Table 4 shows that the inserted genes of KO4 and KO5 were stably maintained as a chromosomal insertion.

TABLE 4

Stability of chromosomally-integrated genes compared to plasmid-based genes in *E. coli* B[a]

| Recombinant | Percentage retaining traits production (number of generations) | |
|---|---|---|
| KO4 | 100 (38.5) | 100 (68.5) |
| KO5 | 100 (38.7) | 100 (68.7) |
| Tc *E. coli* B (pLOI297) | 100 (37.3) | 97 (67.3) |

[a]Transformed *E. coli* B were grown at 30° C. in Luria broth containing 10% (w/v) glucose without antibiotic selection. Tc resistance and ethanol genes were coordinately lost from the plasmid-based construct.

Strains KO4 and KO5 in which the genes for ethanol production have been integrated into the chromosome are superior to the prior construct with plasmid pLOI297, see Alterthun, F., and L. O. Ingram [1989] *Appl. Environ. Microbiol.* 55:1943–1948, in terms of retention of the recombinant trait, ethanol production. Even when the rate of plasmid loss is low, as in *E. coli* strains carrying pLOI297, strains carrying integrated exogenous genes according to the present invention offer considerable advantages over comparable plasmid-based strains for the purpose of commercial ethanol production which involves the scaling up of small cultures to millions of gallons of fermentation broth.

Effect of recA mutation: A recA mutation was also introduced into KO4 and KO11 so that these strains could be used as hosts for recombinant plasmids. The resulting strains were designated KO10 and KO12, respectively. The recA mutation did not affect the production of acetic,, lactic, or succinic acids but did reduce growth and slow fermentation (Table 2) in the recA, frd mutant (KO12). The basis of this effect is unknown, and it may represent secondary mutations which have been created during construction.

Embodiment relating to ethanologenic *Klebsiella oxytoca:* A further illustrative application of the present invention is provided by the integration of *Z. mobilis* genes for ethanol production into the chromosome of *K. oxytoca.* This can be carried out, for example, by a recombination protocol analogous to that described above for E. coli. K. oxytoca and E. coli are closely related, and therefore DNA fragments carrying the Z. mobilis pyruvate decarboxylase and alcohol dehydrogenase (PET) genes within the E. coli pfl gene can be used as a source of DNA to promote the desired recombination event. Briefly, E. coli plasmid or chromosomal DNA carrying both the PET genes and a selectable marker (such as cat) within the pfl gene are digested with restriction enzymes which cut within the pfl gene only. The resulting fragments are circularized and used as transforming DNA for integration experiments as described above for E. coli. Screening of transformants for the presence of the selectable marker and the absence of transforming plasmid allows selection of bacteria in which the transforming DNA has become integrated into the host plasmid. The preparation of recombinant K. oxytoca containing stably integrated PET genes is further illustrated in Example 9 below.

Genes that can be chromosomally inserted according to the present invention: The present invention can be practiced using genes other than the specific adh and pdc genes exemplified herein. It is now well established that the enzymes of glycolysis exhibit a great deal of conservation of primary sequences. See, for example,, Conway, Sewell, and Ingram [1987] J. Bacteriol. 169: 5653–5662. This high level of conservation enables those skilled in the art to isolate functionally equivalent,, genetically related enzymes from other organisms using primary information from one or more members of an enzyme family. Indeed, just such an approach has been used successfully to clone the pyruvate decarboxylase gene from maize using the current inventors' information on the Z. mobilis pdc and the pdc of S. cerevisiae to design a DNA probe. See Kelly, P. M. [1989] Plant Molecular Biology 13:213–222. Alternative strategies using entire genes as probes can also be used. Thus, for purposes of this invention, it does not matter if the pyruvate decarboxylase activity is provided by a gene from Z. mobilis, as exemplified in the subject invention, or from genes which specify the same enzymatic activity from corn (which has been cloned and sequenced), yeasts or another organism. Also, in order to practice the invention, it does not matter if the alcohol dehydrogenase activity is provided from a gene from a horse, yeast, human or insect, or from another bacterial gene. Since expression of alcohol dehydrogenase activity can be observed directly on aldehyde indicator plates, sequence information would not necessarily be the best approach to the isolation of additional genes encoding proteins which exhibit this enzymatic activity. However, whether or not sequences are to be used for such isolation is not really critical. Indeed, many alcohol dehydrogenase genes are already in hand and well described in many papers.

Z. mobilis contains two genes encoding functional alcohol dehydrogenase genes. The one which has been exemplified here, adhB, is evolutionarily related to a butanol (alcohol) dehydrogenase from Clostridium acetobutylicum, propanediol (alcohol) oxidoreductase from E. coli, and ADHIV alcohol dehydrogenase from Saccharomyces. All have been clones and sequenced. The second Z. mobilis gene encoding alcohol dehydrogenase, adhA, is a zinc alcohol dehydrogenase and has recently been cloned and sequenced by us. This adhA is evolutionarily related to the typical alcohol dehydrogenases described in animals, plants, and the dominant gene in yeasts based upon comparisons of primary structure deduced from nucleotide sequences which are available for all. We have found that this adhA gene substitutes quite nicely for the original adhB gene, as expected pursuant to the present invention.

The synthesis of a protein with pyruvate decarboxylase activity (pyruvate converted to acetaldehyde plus carbon dioxide) can be observed directly on aldehyde indicator plates. The expression of alcohol dehydrogenase activity can also be directly observed on aldehyde indicator plates. Therefore, sequence information would not necessarily be the best approach to locating other adh or pdc genes, although, as described above, sequence information from our work was used recently to isolate the corn pdc gene. Thus, many other pdc and adh genes which provide a functional equivalent can be isolated from other organisms. It is entirely predictable that these other genes would be suitable replacements for the Z. mobilis pdc and adh genes available for use, and other such genes can be identified either by use of the current genes as probes or, more preferably, by observing activity on indicator plates.

More generally, many genes other than ethanol-production genes could be incorporated into a chromosome and expressed according to the present invention. These include essentially any desired polypeptide that can be expressed in a recombinant host, for example, are genes encoding insulin, growth hormones, and commercially important enzymes.

Utility of exemplary bacteria: Certain bacteria and other simple organisms are capable of actively metabolizing a wide variety of substrates, including hexoses, pentoses, and lactose. This characteristic makes E. coli an attractive host for recombinant DNA production methods. The invention described here permits the use of recombinant bacterial strains for the economical production of ethanol from a variety of biomass sources, particularly from under-utilized sources of biomass such as hemicellulose (comprising xylose, arabinose, and other sugars), which represents a major portion of wood and inedible plant parts, and whey (lactose). Also, organisms with special capabilities, such as production of extracellular enzymes for the degradation of complex polymers, can be converted to ethanol producers according to the present invention.

Thus, one aspect of the present invention provides an improved organism for the production of ethanol. An E. coli cell has been transformed such that Z. mobilis genes coding for adh and pdc have been incorporated into the host chromosome. In the past, ethanol-production capability has been conferred on E. coli by transformation with a plasmid comprising the two genes needed for ethanol production. The success of these previous transformations resulted from the very high levels of the ethanol-producing enzymes which were made from multiple copies of the genes, typically, 30 to 300 copies per cell.

The initial constructs described here in which single copies of pdc and adh genes were integrated into the host chromosome provided insufficient levels of PDC and ADH to divert metabolism to ethanol and duplicate the level of functionality provided by multiple copies of these genes on a plasmid. Subsequently, spontaneous or induced mutations described above produced cells which simultaneously increased expression of all chromosomally-integrated genes, including that for chloramphenicol resistance, when present, and those for ADH and PDC. These mutants produce high levels of ethanol-production enzymes and are thus functionally equivalent to previous bacteria containing multi-copy plasmids. In the case of spontaneous mutations in a strain carrying a Cm-resistance marker gene as well as ethanol genes, the result whereby increased expression of the Cm-resistance gene also indicated increased expression of the ethanol-related enzymes is particularly surprising because the Cm-resistance gene can include its own promoter and can even be downstream from a transcription terminator of an adhB gene.

Another aspect of this invention concerns the use of the recombinant ethanol-producing bacteria for the efficient production of recombinant proteins; that is, the recombinant cells can be further transformed with genes coding for useful proteins. These additional genes can also be incorporated into a chromosome, or they can be plasmid-borne. Indeed, since high-level expression of the integrated (in this example, ethanol-production) genes, in accordance with the present invention, obviates the need for a plasmid to carry them, recombinant cells of the present invention are particularly well-suited to receive and maintain additional genes carried on a plasmid. An additional mutation, such as a recA mutation, that inhibits homologous recombination will enhance the environmental safety of such hosts in the context of recombinant protein production.

It should be noted that the accumulation of organic acids from sugar metabolism is generally regarded as a consequence of fermentation during anaerobic growth. But appreciable quantities of acetate are generally produced by E. coli even during rapid agitation under aerobic: conditions. The production of acetate is progressive from the earliest stages of growth and is not limited to the later stages, when cell density is high. This acid production from glucose even under aerobic conditions serves to limit growth in broth and on solid medium, as demonstrated by the increased final cell density in medium supplemented with phosphate buffer.

The conversion of a host organism to ethanolic fermentation can be used to enhance the production of a variety of recombinant products. The maintenance of function in these products is related to the pH of the broth during growth in dense culture. The extent of this acidification per unit of cell protein is minimized by the production of ethanol rather than of organic acids. Oxygen transfer is frequently a major limitation during the growth of dense cultures of microorganisms, and it is this limitation which results in acid production and pH drift of the growth medium. In recombinants producing ethanol as a fermentation product, the ethanologenic enzymes divert part of the pyruvate from glycolysis to acetaldehyde and reoxidize NADH to produce ethanol, a less damaging product of metabolism. Strains containing both functional respiratory chains for oxidative phosphorylation and ethanol-production enzymes can be grown to even higher cell densities because of the operation of both systems during the regeneration of NAD$^+$ and a reduction in acidic waste products. Such inherent flexibility results in less stringent process-control requirements, as well as increased yields of recombinant products.

The ethanol-producing bacterial strains of this invention are thus superior hosts for production of recombinant proteins under anaerobic conditions with minimal acid production. Many recombinant proteins contain cysteine or disulfide bridges, and proper folding or reactions of these is an essential feature to form the active enzyme. Since formation of disulfide bonds is promoted by oxygen, synthesis of such proteins under anaerobic conditions provides less opportunity for improper folding prior to isolation and folding under controlled conditions, potentially resulting greater recovery of biologically active product.

From the foregoing it should be readily apparent to one skilled in the art that the ability conferred by the present invention, to transform genes coding for a protein or an entire metabolic pathway onto a chromosome, is extremely useful. Envisioned in this regard, for example, is the application of the present invention to a variety of situations where genes from different genetic loci are placed on a chromosome. The placement of genes coding for ethanol production is only one example of this novel inventive concept. Pursuant to the principles described here, genes coding for alcohol dehydrogenase activity from a variety of organisms can be combined with genes coding for the pyruvate decarboxylase activity from a variety of organisms in order to create the desired pathway. Genes coding for proteins needed for other pathways could also be incorporated chromosomally. It should also be apparent to one skilled in the art that, f or the ethanolic pathway described here, it is not necessary that the genes coding for alcohol dehydrogenase and pyruvate decarboxylase activities be under common control.

The present invention is further described below with regard to the following illustrative examples.

EXAMPLE 1

Construction of Integration Plasmids Containing E. coli Pyruvate Formate-Lyase Gene The following materials and methods were used throughout the present examples unless otherwise stated. E. coli TC4 was used for all genetic constructions. See Conway, T., Y. A. Osman, J. I. Konnan, E. M. Hoffman, and L. O. Ingram [1987] J. Bacteriol. 169:949–954. Luria broth containing the appropriate selective antibiotic and the indicated concentrations of glucose was used in all growth experiments. Antibiotics were used in the following final concentrations except as noted: ampicillin, 50 µg/ml; chloramphenicol (Cm), 20 µg/ml or 600 µg/ml, as indicated; tetracycline, 12.5 µg/ml. ADH indicator plates containing the Schiff reagent were used to detect aldehyde produced from ethanol by recombinant E. coli expressing ADHII of Z. mobilis. Conway, T., G. W. Sewell, Y. A. Osman, and L. O. Ingram [1987] J. Bacteriol. 169:2591–2597.

Standard procedures were used for plasmid preparation, restriction enzyme digestions, ligations, transformations, and gel electrophoresis. Isolation of restriction fragments for subsequent cloning was accompanied by elution from GTG agarose (FMC BioProducts, ME) using Microfilterfuge tubes (Rainin Instrument Co.).

Figure 2:
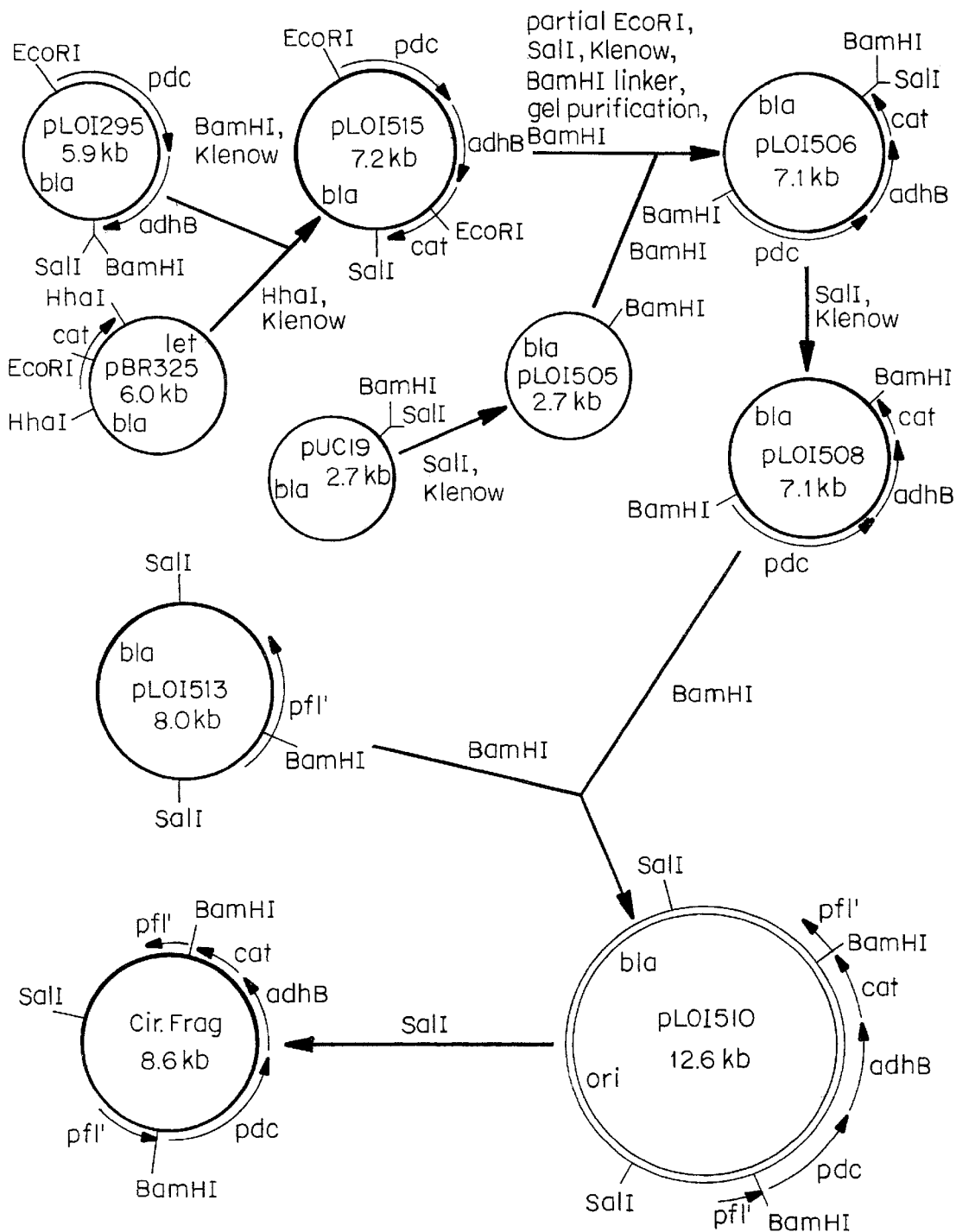
FIG. 2 is a schematic diagram illustrating construction of a plasmid (pLOI510) for the integration of Z. mobilis pdc and adhB genes into a pfl gene of an *E. coli* chromosome using a vectorless, circularized DNA fragment. Abbreviations: Klenow, convert to blunt by filling bases in the overhang region using the Klenow fragment of DNA polymerase I; Cir. Frag., circularized SalI fragment from pLOI510 which has been eluted from an agarose gel and ligated to form closed circles.

The procedure used for construction of integration plasmids containing an E. coli pyruvate formate-lyase gene (pfl) is shown in FIG. 2. Plasmid pHB4 (Sawers et al. [1988], supra) carrying an incomplete pyruvate formate-lyase (pfl) gene of E. coli was partially digested with BamHI, the 5'-protruding ends were filled in with the Klenow fragment of DNA polymerase I, and the fragments were rejoined by ligating to a SAll linker (dCGTCGACG). Those in which the BamHI site outside the pfl gene was replaced by a SalI site were identified by screening of individual transformants. The resulting plasmid, pLOI513, contained two SalI sites which allow removal of the pfl portion of the plasmid from the rest of the plasmid.

A chloramphenicol resistance marker gene was excised as an 1.37-kb HhaI fragment from the plasmid cloning vector, pBR325. See Prentki, P., F. Karch, S. Iida, and J. Meyer [1981] Gene 14:289–299. This HhaI fragment was treated with Klenow polymerase to fill protruding ends and ligated into the Klenow-treated BamHI site downstream from the adhB gene in pLOI295, see Ingram, L. O., T. Conway, D. P. Clark, G. W. Sewell, and J. F. Preton [1987] Appl. Environ. Microbiol. 53:2420–2425, in the same orientation of those of pdc and adhB genes to generate pLOI515. Plasmid pLOI515 was then digested with SalI and partially digested with EcoRI, and, after a Klenow polymerization to generate blunt ends, ligated with BamHI linker (dCCGGATCCGG). Thus ligation mixture was separated on a GTG agarose gel. The fragment carrying promoter-less pdc and adhB genes and the Cm$^r$ gene (with promoter) was isolated and digested with BamHI. The BamHI fragment in which EcoRI and SalI sites were regenerated on each end of the original EcoRI-SalI fragment, was cloned in to the BamHI site in the polylinker of pLOI505 generated by removing SalI site from pUC19 (available from Bethesda Research Laboratories). The SalI site upstream from the Cm$^r$ gene in pLOI506 was removed by digestion with SalI, filling in with Klenow polymerase and religation to generate pLOI508. The 4.6-kb BamHI fragment of pLOI508 was inserted into the BamHI site in the incomplete pfl structural gene carried on plasmid pLOI513. The resultant plasmid pLOI510 was used to introduce the pdc, adhB, and Cm$^r$ genes into the chromosome of *E. coli* strain B (ATCC 11303) by homologous recombination as described below (Example 4).

EXAMPLE 2

Construction of Integration Plasmids Containing *E. coli* Pyruvate Formate-Lyase Gene and Temperature-Sensitive for Plasmid Replication Plasmid pLOI295 was digested with EcoRI and SalI, and the 3.2-kb EcoRI-SalI fragment carrying pdc and adhB genes was treated with Klenow fragment of DNA polymerase to produce blunt ends. This blunt-ended fragment was ligated into the Klenow-treated BamHI site of pLOI513 carrying the incomplete pfl gene in the same orientation with respect to transcription to give pLOI542. pLOI542 was then digested with SalI and the 7.2-kb SalI fragment was ligated to SalI site in the polylinker of pMAK705, see Hamilton, C. M., M. Aldea, B. K. Washburn, P. Babitzke, and S. R. Kushner [1989] *J. Bacteriol.* 171:4617–4622, containing the temperature-sensitive replicon and Cm$^r$ gene (FIG. 1). The resultant plasmid pLOI543 was introduced into the *E. coli* chromosome by homologous recombination (see Example 3 below).

EXAMPLE 3

Chromosomal Integration in *E. coli* B of *Z. mobilis* pdc and adhB Genes with Loss of an Associated Antibiotic Resistance Gene The recombinant plasmid pLOI543, which replicates at 30° C., but not at 44° C., was used to transform *E. coli* B with the Cm$^r$ gene to give it resistance to chloremphenicol. Transformed cells were grown at 44° C. in 100 ml Luria broth containing 20 µg/ml chloramphenicol and 5% (w/v) glucose for 24 hours to select for integration of the plasmid into the chromosome. A portion (0.1 ml) of this culture was diluted, and 0.1 ml of the diluted cell suspension was used to inoculate 100 ml of Luria broth containing 5% (w/v) glucose without chloramphenicol. The culture was grown at 30° C. for 12 hours to allow excision. Two or more cycles of growth were carried out by diluting a portion (0.1 ml) of the culture and inoculating into 100 ml of fresh medium. A diluted cell suspension of the 12-hour culture was then used to inoculate Luria broth containing 5% (w/v) glucose and incubated at 44° C. to eliminate plasmid. Finally, single colonies were isolated by plating serial dilutions of the culture onto Luria agar plates containing 2% (w/v) glucose and growing them at 30° C. Single colonies appearing on the plates were screened for ethanol-production genes by using aldehyde indicator plates and for loss of plasmid as sensitivity to chloramphenicol. Two clones were selected which were sensitive to chloramphenicol but contained the ethanol-production genes, strains KO1 and KO2. These clones produced pink colonies on aldehyde indicator plates.

EXAMPLE 4

Chromosomal Integration in *E. coli* B of *Z. mobilis* pdc and adhB Genes with Retention of an Associated Antibiotic Resistance Gene Plasmid pLOI510 was digested with SalI and the 8.6-kb SalI segment containing an incomplete pfl gene was circularized by self-ligation at a low DNA concentration. The covalently closed DNA fragment lacked sequences allowing autonomous replication. *E. coli* B was transformed with the ligation mixtures by selection for resistance to 20 µg/ml chloramphenicol. Expression of adhB gene in chloramphenicol resistant transformants was confirmed by plating colonies from chloramphenicol plates to ADH indicator plates. A single clone was selected for further characterization, designated strain KO3. The lack of plasmid-borne gene for adh or for chloramphenicol resistance was confirmed by the lack of transformants from DNA preparations and by direct analysis on agarose gels. This clone produced pink colonies on aldehyde indicator plates.

EXAMPLE 5

Generation and Detection of Mutations that Increase Expression of *Z. mobilis* pdc and adhB Genes in the Absence of a Selectable Marker Gene In Example 3, chromosomal integration in *E. coli* B of *Z. mobilis* pdc and adhB genes was carried out under conditions that resulted in loss of the antibiotic, resistance gene that was associated with those ethanol genes on the DNA segment used to transform the host cell. Strain KO2, resulting from the procedure of Example 3, was mutagenized with methyl methane sulfonate under standard conditions well known in the art of bacterial genetics. Surviving mutagenized cells (about 4–8×10$^4$) were plated on aldehyde indicator plates at approximately 200 to 400 colonies per plate. Four dark red clones indicative of increased ADHII expression were isolated and tested for ethanol production as described in Example 8 below. Of these mutants, the one with the highest yield in ethanol production was designated as strain KO20.

EXAMPLE 6

Selection for Mutations that Increase Expression of *Z. mobilis* pdc and adhB Genes by Selection for Increased Expression of an Associated Antibiotic Resistance Gene In Example 4, chromosomal integration in *E. coli* B of *Z. mobilis* pdc and adhB genes was carried out under conditions that resulted in retention of the antibiotic resistance gene that was associated with those ethanol genes on the DNA segment used to transform the host cell. A series of dilutions of strain KO3, which resulted from the procedure of Example 4, were plated on Luria agar plates containing 2% glucose and 600 µg/ml chloramphenicol. Large, fat colonies were observed after overnight incubation, at a frequency of approximately 1 per 100,000 plated cells. These large colonies produced ethanol and tested bright red on alcohol indicator plates. Two strains were investigated further, strains KO4 and KO5.

EXAMPLE 7

Insertion of recA and frd Mutations

The recA mutation in *E. coli* strain JC10240 was transferred to strains KO4 and KO5 by conjugation with selection for resistance to both Cm and tetracycline (nearby Tn10). Co-inheritance of the recA phenotype was confirmed by increased UV sensitivity.

An *E. coli* Hfr strain capable of mobilizing the frd mutation was constructed by transducing the frd deletion mutation from DW12 [zid::Tn10, Δ(frdABCD)] into strain KL282 with selection for Tn10. See Blaut, M., K. Whittacker, A. Valdovinos, B. A. C. Ackrell, R. P. Gunsalus and G. Cecchini [1989] *J. Biol. Chem.* 264:13599–13604. frd mutants were identified among the tetracycline-resistant transductants by loss of fumarate reductase activity. The resulting Hfr strain, SE1706, was used to conjugate the frd deletion into strain KO4.

Tn10 was deleted from constructs by selection on a modified fusaric acid medium. See, e.g., Maloy, S. R., and W. D. Nunn [1981] *J. Bacteriology* 145:1110–1112. This medium contained per liter:15 g agar, 5 g tryptone, 5 g yeast extract, 20 g glucose, 10 g NaCl, 50 mg chlortetracycline, 10 g $NaH_2PO_4$, 12 mg fusaric acid, and 10 mM $ZnCl_2$. Stocks of chlortetracycline (12.5 mg/ml) and fusaric acid (1 mg/ml) were prepared in 70% ethanol. Complex medium components containing chlortetracycline, sodium phosphate and zinc chloride were autoclaved separately and mixed after cooling. Antibiotics in 70% ethanol are self-sterilizing. For selection of Tn10 loss, serial dilutions of log phase cultures were spread on fusaric acid plates and incubated overnight at 37° C. Resulting colonies were streaked for isolation on additional fusaric acid plates and tested for the loss of tetracycline resistance. Three strains were constructed KO10 (recA), KO11 (frd), and KO12 (recA, frd).

EXAMPLE 8

Characterization of Ethanol Gene Expression

Fermentation experiments: Fermentations were carried out in Luria broth supplemented with 10% (w/v) glucose or 8% (w/v) xylose. Fleakers (500-ml, Fisher Scientific Company, Orlando, Fla.) containing 350 ml of the medium were equipped with a pH electrode, gas outlet, and sampling port through appropriately drilled rubber caps. A Jenco model 3671 pH controller (Whatman Lab Sales, Hillsboro, Oreg.) was used to maintain a pH of 6.0 by the addition of base (2N KOH). Batch fermentations were carried out in duplicate at 30° C. and were stirred continuously by a 1.25 inch star-shaped magnetic bar (100 rpm).

Inocula were grown overnight at 30° C. from isolated colonies in unshaken flasks. Fermentations were inoculated to an initial $O.D._{550nm}$ of approximately 1.0 (330 mg dry weight of cells/liter).

Cell growth was monitored turbidimetrically at 550 nm using a Bausch and Lomb Spectronic 70 spectrophotometer. Ethanol was measured by gas-liquid chromatography as described, for example, by Dombek, K. M., and L. O. Ingram [1986] *Appl. Environ. Microbiol.* 51:197–200. Values for conversion efficiency were corrected for fermentation volume changes caused by the addition of base and assumed that all sugar initially added had been metabolized. Volumetric productivities and specific productivities were estimated during the early stages of fermentation (6 to 24 hours) and represent maximum values. All fermentation data in tables and in figures represent averages from two or more batch fermentations.

Analysis of volatile and non-volatile acids in the culture: Samples were removed for organic acid analyses after 72 hours of fermentation. Volatile and non-volatile acids were measured by gas-liquid chromatography with a Gow-Mac Series 580 gas chromatograph (Gow-Mac Instrument Company, Bridgewater, N.J.) connected to a Hewlett-Packard 3390A integrator. Nonvolatile acids were converted to methyl esters prior to analysis.

Sodium dodecyl sulfate polyacrylaside gel electrophoresis (SDS-PAGE): Cells were grown for 24 hours under the conditions of the fermentation experiments, chilled to 0° C., harvested by centrifugation (7,000×g, 10 minutes), washed twice with ⅓ volume of 5 mM sodium phosphate buffer (pH 6.5) containing 10 mM 2-mercaptoethanol, and stored frozen at −20° C. Cell pellets were resuspended in an equal volume of buffer and broken by two passages through a French pressure cell at 20,000 psi. Membranes were removed by centrifugation for 90 minutes at 100,000×g. The supernatants were separated with a Biorad Mini-Protein II electrophoresis unit (Biorad Laboratories, Richmond, Calif.) using an 8% acrylamide denaturing sodium dodecyl sulfate gel. Protein was measured with the Bradford reagent. See Bradford, M. M. [1979] *Mol. Gen. Genet.* 181:548–551. Approximately 20 μg of protein was loaded into each lane.

Enzyme activity: PDC activity was measured in heat-treated French press extracts as described, for example, by Conway, T., Y. A. Osman, J. I. Konnan, E. M. Hoffmann and L. O. Ingram [1987] *J. Bacteriol.* 169:949–954. Heat treatment was used to inactivate competing native enzymes which complicate measurements of PDC in recombinant *E. coli*.

EXAMPLE 9

Ethanol Production from Cellobiose, Amorphous Cellulose, and Crystalline Cellulose by Recombinant *Klebsiella oxytoca* Containing Chromosomally Integrated *Z. mobilis* Genes for Ethanol Production Three approaches were used to integrate PET genes into the chromosome of *K. oxytoca* M5A1 (Orsdov [1984] p. 461–465, in N. R. Kreig and J. G. Holt (ed.), Bergey's manual of systematic bacteriology, vol. 1. The Williams and Wilkins Co., Baltimore). Since *K. oxytoca* and *E. coli* are closely related, the *E. coli* pfl gene was used a potential source of homologous DNA to promote recombination analogous to the method used for *E. coli* (Ohta et al. *Appl. Environ. Microbiol.* 57:893–900). SalI fragments of 8.6 kbp were purified from pLOI510 which contained PET genes and cat within the pfl gene of *E. coli*. This fragment (lacking genes involved in replication) was circularized by ligation and transformed into M5A1 to allow direct selection for integration. A shorter 5 kbp PstI fragment containing only a small amount of flanking *E. coli* pfl was used in a similar manner. In the third approach, homologous *K. oxytoca* M5A1 DNA (2 kbp random Sau3A fragments) was ligated to a 4.6 kbp BamHI fragment containing only the PET genes with cat (no *E. coli* DNA) and used for transformation. Integrated strains were recovered from all three approaches by selection on Luria broth plates containing 2% glucose and 20 μg Cm/ml. Three integrated clones were recovered with the SalI fragment, two with the PstI fragment and one with the BamHI fragment.

After overnight growth in liquid culture, 0.1 ml of stationary phase cells was spread on plates containing 600 μg Cm/ml and 2% glucose to select for high level expression.

Single large colonies were retained from each independent integration event and named according to the restriction site used for construction, i.e., S1, S2, S3, P1, P2, and B1. These clones were tested for the presence of plasmids by transformation of miniscreen DNA and for expression of PET genes on aldehyde indicator plates (Table 5). Putative integrated strains found to contain plasmid-borne cat genes were discarded after digesting miniscreen DNA to confirm the presence of pLOI510 (presumably a low level contaminant of gel-purified fragments). The parent organism and M5A1 (pLOI555), an excellent ethanol producer, were included as negative and positive controls, respectively. Two clones expressed the ethanol genes at levels nearly equivalent to that of that of M5A1(pLOI555), strains B1 and P2.Plasmid LOI510, containing PET genes and cat within the E. coli pfl gene was digested with SalI, or Pst1, circularized and transformed into K. oxytoca strain M501. See Wood et al., Appl. Environ. Microbiol. 58:2103 (1992), which is herein incorporated by reference. Additionally, homologous K. oxytoca M5A1 DNA prepared by Sau3A digestion was ligated to a 4.6 kb BamH1 fragment containing only the PET and cat genes was also used for transformation. Recombinants were initially selected using 20 μg chloramphenicol/ml and expressed low levels of Z. mobilis enzymes. As with E. coli (Ohta et al. [1991] Appl. Environ. Microbiol. 57:893–900), expression was boosted by direct selection of mutants with resistance to 600 μg chloramphenicol/ml. A single clone expressing high level resistance was retained for each independent integration event.

Fermentations were carried out in 500-ml Fleakers which served as pH stats (350 ml working volume) essentially as described previously (Beall et al., Biotechnol. & Bioeng. 38:296–303 (1991)). Luria broth containing either 10% glucose or 10% cellobiose was tested at 30° C., pH 6.0, 100 rpm. Inocula for fermentations were grown at 30° C. overnight in unshaken, 250-ml flasks containing 50 ml of Luria broth (4% glucose). After mixing, cell densities were measured at 550 nm and used to calculate the volume required to provide an initial density of 0.32 mg cell dry weight/ml (O.D. 550 nm of 1.0). Cells were harvested from this volume by centrifugation and resuspended in a portion of the broth from each respective pH-stat to start fermentation.

Sugars were sterilized separately by filtration. Cellulose fermentations contained 50 g/liter SOLKA FLOC SW40 (James River Corporation, Saddle Brook, N.J.) and were carried out at 35° C. Cellulose was sterilized by autoclaving as a dry powder. For investigations of cellulose fermentation using commercial enzymes, CYTOLASE or MULTIFECT, was added at the time of inoculation.

Samples were removed for the determination of cell mass (O.D. 550 nm) and ethanol (gas liquid chromatography; Beall et al., supra) . Ethanol concentrations are expressed as g/liter. Ethanol yields were corrected for dilution by the addition of base during fermentation and computed on the basis of total sugar or cellulose initially present. No corrections were made for residual carbohydrates. Maximum theoretical yields from glycolysis and fermentation are 0.51 g ethanol/g glucose, 0.536 g ethanol/g cellobiose,, and 0.56 g ethanol/g cellulose. Except as indicated, results presented are an average of 2 or more fermentations.

TABLE 5

Fermentation of 10% glucose (48 hours) by strains of M5A1 containing integrated pet genes.

| Strain[a] | Base (mM/liter) | Cell Mass[b] (g/liter) | Ethanol (g/liter) | Aldehyde[c] Plates | Plasmid[d] |
|---|---|---|---|---|---|
| M5A1 | 108 | 3.2 | 15 | – | – |
| M5A1 (pLOI555) | 91 | 5.1 | 45 | ++++ | + |
| S1 | 120 | 2.9 | 37 | + | – |
| S2 | 171 | 3.2 | 44 | ++ | – |
| S3 | 97 | 2.4 | 37 | ++ | – |
| P1 | 120 | 2.0 | 38 | ++ | – |
| P2 | 91 | 3.7 | 44 | +++ | – |
| B1 | 63 | 4.0 | 47 | ++++ | – |

[a]Values reported are from a single experiment although many were reproduced and averaged in subsequent investigations.
[b]Cell mass was calculated from the maximal O.D. at 550 nm (approx. 0.32 g dry weight/liter per O.D. unit).
[c]Comparative rate of color development on aldehyde indicator plates at 30° C. was used as a relative measure of expression from the pet operon.
[d]Small scale preparations of DNA were examined on agarose submarine gels and tested for their ability to transfer antibiotic resistance to E. coli DH5α during transformation.

Comparison of glucose fermentation by integrated strains to M5A1(pLOI555): After 48 hours, high levels of ethanol equivalent to M5A1(pLOI555) were produced by 4 strains containing PET integrations (Table 5). The two which produced the lowest levels of acidic co-products also grew to the highest densities. These strains, P2 and B1, were selected for further investigation.

Fermentation of glucose and cellobiose by strains P2 and B1. Strains P2 and B1 were investigated for their ability to ferment 10% glucose and 10% cellobiose (table 6). During glucose fermentation (FIG. 5), both integrated strains produced 3 times more ethanol than the parent organism, M5A1, but were slightly inferior to M5A1(pLOI555) (plasmid-borne PET genes) in yield, and in volumetric productivity. Unexpectedly, integration and high level expression of PET genes in strain B1 was accompanied by a loss of ability to ferment cellobiose. Strain P2, however, grew well and produced ethanol from cellobiose (FIG. 6) with 96% of the maximum theoretical yield.

Figure 5:
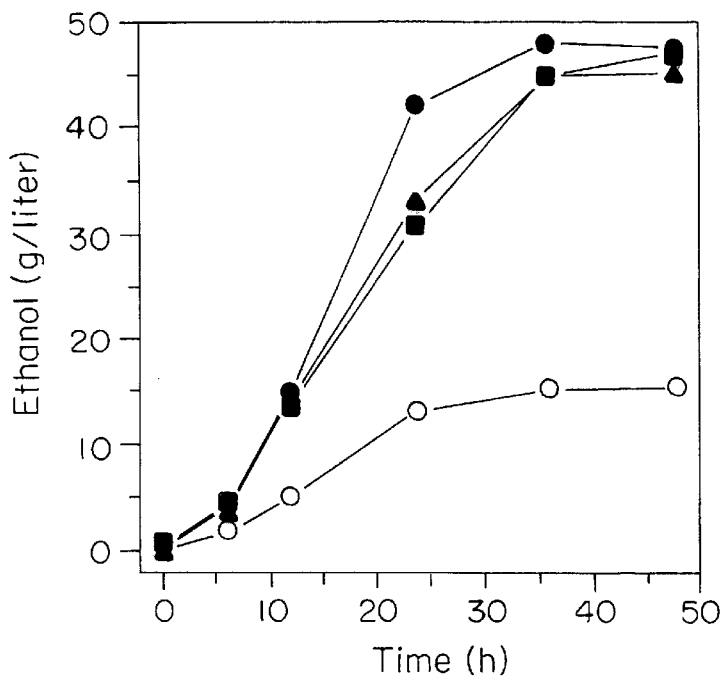
FIGS. 5 and 6 illustrate the ethanol production by recombinant strains of *K. oxytoca* M5A1.
Figure 6:
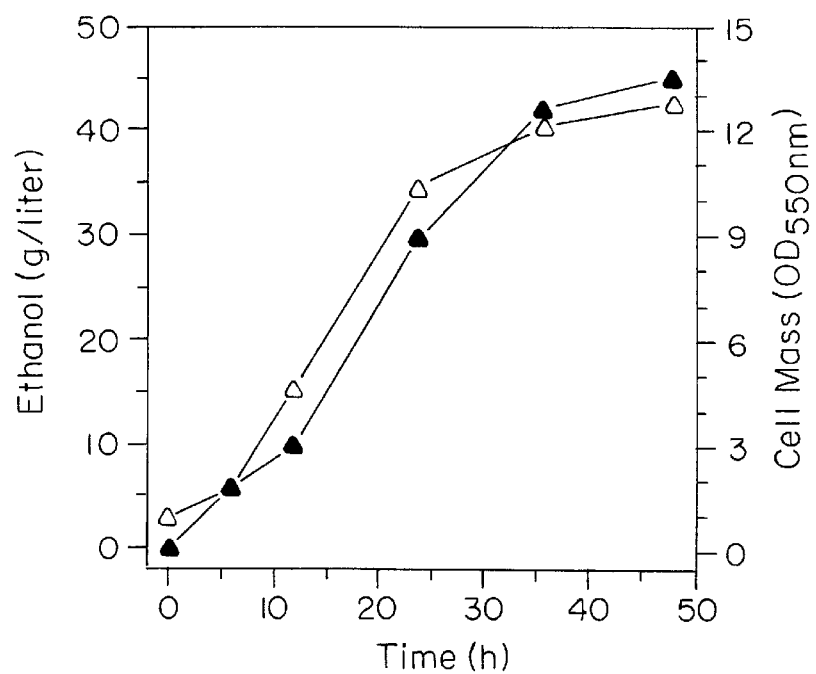

FIGS. 5 and 6 thus illustrate the ethanol production by recombinant strains of K. oxytoca M5A1. FIG. 5 illustrates the production from glucose (100 g/liter). Symbols: ●, strain M5A1(pLOI555); ▲, strain P2 containing integrated PET genes; ■, strain B1 containing integrated PET genes; ○, M5A1 control. FIG. 6 illustrates the production from cellobiose (100 g/liter) fermentation by strain P2. Symbols: ▲, ethanol; Δ, cell mass.

It should be understood that the examples and embodiments described herein are for illustrative purposes only and that various modifications or changes in light thereof will be suggested to persons skilled in the art and are to be included within the spirit and purview of this application and the scope of the appended claims.

TABLE 6

Ethanol production by recombinant strains of K. oxytoca M5A1.

| Organism[a] | Substrate | Additives[b] | Volumetric Productivity (g/liter/h) | Max. EtOH (g/liter) | Yield (g/g S) | % Theoretical[e] Yield |
|---|---|---|---|---|---|---|
| M5A1 | 10% glucose | none | 0.72 | 16.2 | 0.17 | 33 |
| M5A1(pLOI555) | " | " | 2.1 | 48.0 | 0.50 | 99 |
| P2 | " | | 1.6 | 46.4 | 0.46 | 90 |
| B1 | " | " | 1.5 | 47.6 | 0.49 | 96 |
| P2 | 10% cellobiose | " | 1.5 | 45.2 | 0.49 | 96 |
| B1 | " | " | 0.1 | 1.2 | 0.01 | 2 |
| P2 | none | " | 0.04 | 1.0 | — | — |
| P2 | none | 10% CYTOLASE | 0.12 | 4.7 | — | — |
| P2 | none | 10% MULTIFECT | 0.06 | 5.2 | — | — |
| P2 | 5% SOLKA FLOC SW40 | no enzyme | 0.05 | 2.0 | 0.04 | 8 |
| P2 | 5% SOLKA FLOC SW40 | 0.1% CYTOLASE | 0.08 | 2.3 | 0.07 | 12 |
| P2 | " | 0.5% CYTOLASE | 0.13 | 7.0 | 0.14 | 26 |
| P2 | " | 1.0% CYTOLASE | 0.18 | 8.7 | 0.18 | 32 |
| P2 | " | 5.0% CYTOLASE | 0.52 | 16.9 | 0.36 | 64 |
| P2 | " | 10% CYTOLASE | 0.50 | 16.3 | 0.35 | 62 |
| P2 | 5% SOLKA FLOC SW40 | 0.1% MULTIFECT | 0.08 | 3.3 | 0.07 | 12 |
| P2 | " | 0.5% MULTIFECT | 0.18 | 5.9 | 0.13 | 23 |
| P2 | " | 1.0% MULTIFECT | 0.36 | 10.4 | 0.23 | 41 |
| P2 | " | 5.0% MULTIFECT | 0.76 | 23.8 | 0.51 | 92 |
| P2 | " | 10% MULTIFECT | 0.86 | 32.5 | 0.69 | 123 |

[a]Glucose and cellobiose fermentations were carried out at 30° C.; other fermentations were carried out at 35° C.
[b]Enzymes were added at the time of inoculation.
[c]Computed for the time period between 6 and 24 hours.
[d]Corrected for dilution by the addition of base during fermentation. S (substrate) refers to glucose, cellobiose or SOLKA FLOC SW40.
[e]Based on a maximum theoretical yield of 51 g ethanol/100 g glucose, 53.5 g ethanol/100 g cellobiose, and 28 g ethanol/50 g cellulose. Values were not corrected for residual substrate.

What is claimed is:

1. A recombinant host cell comprising:
   a) a heterologous nucleic acid molecule comprising a first coding sequence, a promoter and a second coding sequence wherein said second coding sequence is under transcriptional control of said promoter; wherein said heterologous nucleic acid molecule is integrated into the chromosome of the host cell such that said first coding sequence is under transcriptional control of an endogenous promoter of the host cell; and
   b) said recombinant host cell is further characterized by a mutation that causes increased expression of said first and second coding sequences.

2. A recombinant host cell according to claim 1, wherein said first coding sequence encodes a plurality of polypeptides.

3. A recombinant host cell according to claim 2, wherein said second coding sequence encodes a selectable marker protein.

4. A recombinant host cell according to claim 3, wherein expression of said selectable marker protein confers antibiotic resistance upon said host cell.

5. A recombinant host cell according to claim 4, wherein expression of said selectable marker protein confers chloramphenicol resistance upon said host cell.

6. A recombinant host cell according to claim 1, wherein said host cell is a bacterium.

7. A recombinant host cell according to claim 6, wherein said host cell is an enteric bacterium.

8. A recombinant host cell according to claim 7, wherein said enteric bacterium is selected from the group consisting of Erwinia, Escherichia and Klebsiella.

9. A recombinant host cell according to claim 8, wherein said enteric bacterium is an *Escherichia coli* cell.

10. A recombinant host cell according to claim 1, wherein said endogenous promoter is a strong promoter.

11. A recombinant host cell according to claim 10, wherein said heterologous nucleic acid molecule is under transcriptional control of an endogenous promoter of a gene that is expressed at substantially the level at which the pyruvate formate-lyase (pfl) gene is expressed in said host cell.

12. A recombinant host cell according to claim 11, wherein said endogenous promoter is a promoter of a pyruvate formate-lyase (pfl) gene.

13. A recombinant host cell according to claim 1, wherein said first coding sequence encodes an alcohol dehydrogenase or a pyruvate decarboxylase or both.

14. A recombinant host cell according to claim 13, wherein said alcohol dehydrogenase and said pyruvate decarboxylase are encoded by genes from *Zymomonas mobilis*.

15. A recombinant host cell according to claim 14, wherein said host cell is an *Escherichia coli* cell, said endogenous promoter is a promoter of the pyruvate formate-lyase (pfl) gene, and said cell is able to produce ethanol by fermentation of glucose or xylose with a theoretical yield corresponding to conversion of at least 90% of added sugar to ethanol.

16. A recombinant host cell according to claim 15, wherein said host cell comprises a mutation that impairs succinate production.

17. A recombinant host cell according to claim 16, wherein said mutation that impairs succinate production comprises a mutation in a fumarate reductase (frd) gene.

18. A recombinant host cell according to claim 1, wherein said host cell comprises a mutation that impairs recombination in said host cell.

19. A recombinant host cell according to claim 18, wherein said mutation that impairs recombination comprises a mutation in a recA gene.

20. A recombinant host cell according to claim 1, wherein said heterologous nucleic acid molecule cannot replicate as a plasmid in said host cell.

21. The recombinant host cell of claim 1 wherein said heterologous nucleic acid molecule further comprises a transcriptional terminator located between said first coding sequence and said promoter.

22. A process for producing a recombinant host cell that produces high levels of a desired polypeptide, comprising the steps of:

a) transforming one or more host cells with a heterologous nucleic acid molecule comprising a first coding sequence, a promoter and a second coding sequence wherein said second coding sequence is under transcriptional control of said promoter, whereby integration of said heterologous nucleic acid molecule results by means of homologous recombination, such that said first coding sequence is under transcriptional control of an endogenous promoter of the host cell;

b) selecting for one or more host cells produced in step (a) that express the second coding sequence;

c) exposing one or more host cells identified in step (b) to a mutagen under suitable conditions for mutation; and d) screening one or more host cells of step (c) that express said second coding sequence and said first coding sequence at an increased level.

23. The process according to claim 24, wherein a) said nucleic acid molecule is a plasmid comprising a replicon that is temperature-sensitive for replication;

b) said transformation comprises introducing said plasmid into said one or more host cells and growing said one or more host cells under conditions that select for host cells that express said desired polypeptide at a temperature that does not permit replication of said plasmid.

24. A process according to claim 23 wherein said second coding sequence encodes a selectable marker protein.

25. A process according to claim 24, wherein said selectable marker protein confers resistance to chloramphenicol on said host cell.

26. A process according to claim 25, wherein said resistance is at least 20 µg/ml of chloramphenicol.

27. A process according to claim 22, wherein said heterologous nucleic acid molecule further comprises a transcriptional terminator, said transcriptional terminator being located between said first coding sequence and said sequence encoding a selectable marker protein.

28. A host cell produced by the process of claim 22.

29. The recombinant *Escherichia coli* KO4 ATCC 55123.

30. The recombinant *Escherichia coli* KO11 ATCC 55124.

31. The recombinant *Escherichia coli* KO12 ATCC 55125.

* * * * *